US011981672B2

(12) United States Patent
Desantis et al.

(10) Patent No.: US 11,981,672 B2
(45) Date of Patent: May 14, 2024

(54) BI-FUNCTIONAL COMPOUNDS AND METHODS FOR TARGETED UBIQUITINATION OF ANDROGEN RECEPTOR

(71) Applicant: MONTELINO THERAPEUTICS, INC., Southborough, MA (US)

(72) Inventors: Jenny Desantis, Foligno (IT); Roy Joseph Vaz, Southborough, MA (US); Michela Eleuteri, Perugia (IT)

(73) Assignee: Montelino Therapeutics Inc., Southborough, MA (US)

( * ) Notice: Subject to any disclaimer, the term of this patent is extended or adjusted under 35 U.S.C. 154(b) by 0 days.

(21) Appl. No.: 17/931,843

(22) Filed: Sep. 13, 2022

(65) Prior Publication Data

US 2023/0134817 A1 May 4, 2023

Related U.S. Application Data

(60) Provisional application No. 63/243,589, filed on Sep. 13, 2021.

(51) Int. Cl.
*C07D 471/04* (2006.01)
(52) U.S. Cl.
CPC ................. *C07D 471/04* (2013.01)
(58) Field of Classification Search
None
See application file for complete search history.

(56) References Cited

U.S. PATENT DOCUMENTS

| | | |
|---|---|---|
| 6,306,663 B1 | 10/2001 | Kenten et al. |
| 6,888,241 B1 | 5/2005 | Korn et al. |
| 9,993,514 B2 | 6/2018 | Campos et al. |
| 11,098,025 B2 | 8/2021 | Desantis et al. |
| 2014/0356322 A1 | 12/2014 | Crews et al. |
| 2016/0214972 A1 | 7/2016 | Jin et al. |
| 2017/0008904 A1 | 1/2017 | Crew et al. |
| 2017/0183319 A1 | 6/2017 | Tcherkassov et al. |
| 2017/0218353 A1 | 8/2017 | Petter et al. |
| 2017/0327469 A1 | 11/2017 | Crew et al. |
| 2018/0099940 A1 | 4/2018 | Crew et al. |
| 2018/0118733 A1 | 5/2018 | Harling et al. |
| 2018/0134688 A1 | 5/2018 | Casillas et al. |
| 2018/0346461 A1 | 12/2018 | Crew et al. |
| 2019/0192668 A1 | 6/2019 | Mainolfi et al. |
| 2020/0282068 A1 | 9/2020 | Desantis et al. |
| 2021/0292298 A1 | 9/2021 | Desantis et al. |

FOREIGN PATENT DOCUMENTS

| | | |
|---|---|---|
| WO | WO 2014/026198 | 2/2014 |
| WO | WO 2015/120543 | 8/2015 |
| WO | WO 2016/105518 A1 | 6/2016 |
| WO | WO 2017/007612 | 1/2017 |
| WO | WO 2017/176957 A1 | 10/2017 |
| WO | WO 2017/197056 | 11/2017 |
| WO | WO 2018/114781 | 6/2018 |
| WO | WO 2018/213278 | 11/2018 |
| WO | WO 2021/236695 | 11/2021 |

OTHER PUBLICATIONS

Alabi et al., "Major advances in targeted protein degradation: PROTACs, LYTACs, and MADTACs", *J. Biol. Chem.*, 296:100647, (2021).
Antonarakis, et al, "AR-V7 and Resistance to Enzalutamide and Abiraterone in Prostate Cancer," New England, Journal of Medicine, 371(11):1028-1038 (2014).
Bond et al., "Proteolysis targeting chimeras (PROTACs) come of age: entering the third decade of targeted protein degradation", *RSC Chemical Biology*, 2:725-742, (2021).
Chamberlain, et al., "Cereblon modulators: Low molecular weight inducers of protein degradation," *Drug Discovery Today: Technologies*, vol. 31, 2019, pp. 29-34.
Chopra, et al., "A critical evaluation of the approaches to targeted protein degradation for drug discovery", Drug Disc Today: Technologies, 31, pp. 5-13, (2019).
Churcher, I., "Protac-Induced Protein Degradation in Drug Discovery: Breaking the Rules or Just Making New Ones?," *Journal of Medicinal Chemistry*, 61, pp. 444-452, (2018).
Crews, C. M., "Targeting the Undruggable Proteome: The Small Molecules of My Dreams," *Chemistry & Biology*, 17, pp. 551-555, (2010).
Dalal, et al., "Selectively targeting the dimerization interface of human androgen receptor with small-molecules to treat castration-resistant prostate cancer," *Elsevier, Cancer Letters*, 437, pp. 35-43, (2018).
Dalal, et al., "Bypassing Drug Resistance Mechanisms of Prostate Cancer with Small Molecules that Target Androgen Receptor-Chromatin Interactions", *Mal. Cancer Ther.*, 16(10), pp. 2281-2291, (2017).
Dehm, et al., "Alternatively Spliced Androgen Receptor Variants," *Endocr Relat Cancer.*, 18(5): pp. R183-R196, (2011).
Frost, et al., "Potent and selective chemical probe of hypoxic signaling downstream of HIF-a hydroxylation via VHL inhibition", *Nature Communications*, 7:13312; pp. 1-12, (2016).
Han, et al., "Anticancer sulfonamides target splicing by inducing RBM39 degradation via recruitment to DCAF15," *Science*, 356, 397, (2017).

(Continued)

*Primary Examiner* — Joseph R Kosack
(74) *Attorney, Agent, or Firm* — Hoxie & Associates LLC

(57) ABSTRACT

The present invention relates to bi-functional compounds which function to recruit endogenous proteins to an E3 ubiquitin ligase for degradation, and methods for using same. More specifically, the present disclosure provides specific proteolysis targeting chimera (PROTAC) molecules which find utility as modulators of targeted ubiquitination of a variety of polypeptides and other proteins, in particular the androgen receptor of a slice variant of AR which lacks the LBD, labelled as AR-V7, which are then degraded and/or otherwise inhibited by the compounds as described herein.

19 Claims, No Drawings

(56) References Cited

OTHER PUBLICATIONS

Hansen, et al., "Protein Degradation via CRL4CRBN Ubiquitin Ligase: Discovery and Structure-Activity Relationships of Novel Glutarimide Analogs That Promote Degradation of Aiolos and/or GSPT1," *Journal of Medicinal Chemistry*, 61, pp. 492-503, (2018).
Hines, et al., "MDM2-Recruiting PROTAC Offers Superior, Synergistic Antiproliferative Activity via Simultaneous Degradation of BRD4 and Stabilization of p53," *American Association for Cancer Research*, 79, pp. 251-262, (2019).
Hunter, et al., "The inhibitors of apoptosis (IAPs) as cancer targets," *Apoptosis*, 12, pp. 1543-1598, (2007).
International Search Report and Written Opinion of International Application No. PCT/US2020/15922, prepared by the International Searching Authority, dated Mar. 30, 2020, 13 pages.
Itoh, et al., "Double protein knockdown of cIAP1 and CRABP-11 using a hybrid molecule consisting of ATRA and APs antagonist," *Bioorganic & Medicinal Chemistry Letters*, 22, pp. 4453-4457, (2012).
Li, et al., "Discovery of Small-Molecule Inhibitors Selectively Targeting the DNA-Binding Domain of the Human Androgen Receptor," *Journal of Medicinal Chemistry*, 57, 6458-6467, (2014). (correction included).
Li, et al., "Discovery of Small-Molecule Inhibitors Selectively Targeting the DNA-Binding Domain of the Human Androgen Receptor," Journal of Medicinal Chemistry, 57, 6458-6467, (2014). (correction).
Li et al., "Protein degradation technology: a strategic paradigm shift in drug discovery", *Journal of Hematology & Oncology*, 14:138, (2021).
Naito, et al., "SNIPERs—Hijacking IAP activity to induce protein degradation," *Drug Discovery Today: Technologies*, vol. 31, pp. 35-42, (2019).
Ohoka, et al., "In Vivo Knockdown of Pathogenic Proteins via Specific and Nongenetic Inhibitor of Apoptosis Protein (IAP)—dependent Protein Erasers (SNIPERs)," *Journal of Biological Chemistry*, 292(11), 1556-4570, (2017).
Pettersson, et al., "PROteolysis Targeting Chimeras (PROTACs)—Past, present and future," *Drug Discovery Today Technologies*, vol. 31, pp. 15-27, (2019).
PubChem CID 132260110, Date Created: Jan. 29, 2018, Obtained from the Internet: May 27, 2020, 8 pages. URL: <https://pubchem.ncbi.nlm.nih.gov/compound/132260110>.
Rodriguez-Gonzalez, et al., "Targeting steroid hormone receptors for ubiquitination and degradation in breast and prostate cancer," *Oncogene*, 27, pp. 7201-7211, (2008).
Roth et al., "Advances in targeted degradation of endogenous proteins", Cellular and Molecular Life Sciences, 76:2761-2777, (2019).
Shibata, et al., "Development of Protein Degradation Inducers of Androgen Receptor by Conjugation of Androgen Receptor Ligands and Inhibitor of Apoptosis Protein Ligands," *Journal of Medicinal Chemistry*, 61, 543-575, (2018).
Sievers, et al., "Defining the human C2H2 zinc-finger degrome targeted by thalidomide analogs through CRBN," *Science*, 362, (2018).
Skalniak, et al., A therapeutic patent overview of MDM2/X-targeted therapies (2014-2018), *Expert Opinion on Therapeutic Patents*, (2019).
Soares, et al., "Group-Based Optimization of Potent and Cell-Active Inhibitors of the von Hippel-Lindau (VHL) E3 Ubiquitin Ligase: Structure—Activity Relationships Leading to the Chemical Probe (2S,4R)-1-((S)-2-(1-Cyanocyclopropanecarboxamido)-3,3-dimethylbutanoyl-4-hydroxy-N-(4-(4-methylthiazol-5-yl)benzyl)pyrrolidine-2-carboxamide (VH298)," *Journal of Medicinal Chemistry*, 61, 599-618, (2018).
Varfolomeev et al., "IAP Antagonists Induce Autoubiquitination of c-IAPs, NF-κB Activation, and TNFa-Dependent Apoptosis", *Cell*, 131:4; pp. 669-681, (2007).

BI-FUNCTIONAL COMPOUNDS AND METHODS FOR TARGETED UBIQUITINATION OF ANDROGEN RECEPTOR

CROSS-REFERENCE TO RELATED APPLICATIONS

This U.S. application claims priority to, and the benefit of, U.S. Provisional Application Ser. No. 63/243,589, filed on Sep. 13, 2021, the contents of which are hereby incorporated by reference in its entirety.

FIELD OF THE INVENTION

This invention relates to therapeutic compounds and compositions, and methods for their use in the treatment of various indications, including various cancers. In particular, the invention relates to therapies and methods of treatment for cancers such as prostate cancer.

BACKGROUND OF THE INVENTION

Prostate cancer is the most commonly diagnosed malignancy in males in the United States and the second leading cause of male cancer mortality. Numerous studies have shown that the androgen receptor (AR) is central not only to the development of prostate cancer, but also the progression of the disease to the castration resistance state (Taplin, M. E. et al., *J. Clin. Oncol.* 2003 21:2673-8; and Tilley, W. D. et al., *Cancer Res.* 1994 54:4096-4102). Thus, effective inhibition of human AR remains one of the most effective therapeutic approaches to the treatment of advanced, metastatic prostate cancer.

Androgens are also known to play a role in female cancers. One example is ovarian cancer where elevated levels of androgens are associated with an increased risk of developing ovarian cancer (Helzlsouer, K. J. et al., *JAMA* 1995 274, 1926-1930; Edmondson, R. J. et al., *Br. J. Cancer* 2002 86, 879-885). Moreover, AR has been detected in a majority of ovarian cancers (Risch, H. A., *J. Natl. Cancer Inst.* 1998 90, 1774-1786; Rao, B. R. et al., *Endocr. Rev.* 1991 12, 14-26; Clinton, G. M. et al., *Crit. Rev. Oncol. Hematol.* 1997 25, 1-9).

AR belongs to the nuclear hormone receptor family that is activated by androgens such as testosterone and dihydrotestosterone. These androgens, as well as antagonists such as enzalutamide, compete with the androgens that bind to the ligand binding domain (LBD). AR possesses a modular organization characteristic of all nuclear receptors. It is comprised of an N-terminal domain (NTD), a central DNA binding domain (DBD), a short hinge region, and a C-terminal domain that contains a hormone ligand binding pocket (the LBD, which also comprises the hormone binding site (HBS)) and the Activation Function-2 (AF2) site (Gao, W. Q. et al., *Chem. Rev.* 2005 105:3352-3370). The latter represents a hydrophobic groove on the AR surface which is flanked with regions of positive and negative charges— "charge clamps"—that are significant for binding AR activation factors (Zhou, X. E. et al., *J. Biol. Chem.* 2010 285:9161-9171).

The activation of AR follows a well characterized pathway: in the cytoplasm, the receptor is associated with chaperone proteins that maintain agonist binding conformation of the AR (Georget, V. et al., *Biochemistry* 2002 41:11824-11831). Upon binding of an androgen, the AR undergoes a series of conformational changes, disassociation from chaperones, dimerization, and translocation into the nucleus (Fang, Y. F. et al., *J. Biol. Chem.* 1996 271: 28697-28702; and Wong, C. I. et al., *J. Biol. Chem.* 1993 268:19004-19012) where it further interacts with co-activator proteins at the AF2 site (Zhou, X. E. et al. *J. Biol. Chem.* 2010 285:9161-9171). This event triggers the recruitment of RNA polymerase II and other factors to form a functional transcriptional complex with the AR.

In castration-resistant prostate cancer (CRPC), drug resistance can manifest through AR-LBD mutations that convert AR-antagonists into agonists or by expression of AR-variants lacking the LBD. AR is a major driver of prostate cancer and inhibition of its transcriptional activity using competitive antagonists such as enzalutamide and apalutamide remains a frontline therapy for prostate cancer management. Another therapy is abiraterone which is an inhibitor of cytochrome P450 17A1 that impairs AR signaling by depleting adrenal and intratumoral testosterone and dihydrotestosterone. Recent work (Antonarakis, E. S. et al., *New Engl. J. Med.* 2014 37, 1028-1038) has shown that patients on enzalutamide and abiraterone with a splice variant of AR, labelled as AR-V7, had lower PSA response rates, shorter PSA progression-free survival, and shorter overall survival.

AR-V7 lacks the LBD, which is the target of enzalutamide and testosterone, but AR-V7 remains constitutively active as a transcription factor. Accordingly, it is desirable to investigate other approaches to antagonize the AR receptor as well as AR-V7. The common domain between these two proteins is the DBD and compounds have been identified as discussed in Li, H. et al., *J. Med. Chem.* 2014 57, 6458-6467 (2014); Dalal, K. et al., *Mol. Cancer Ther.* 2017 vol. 16, 2281-2291; Xu, R. et al., *Chem. Biol. & Drug Design* 2018 91(1), 172-180; and WO 2015/120543.

Several methods are available for the manipulation of protein levels, including bi-functional proteolysis targeting chimeric molecules (PROTACs) which contain a ligand that recognizes the target protein that is linked to a ligand that binds to a specific E3 ubiquitin ligase. The ensuing bifunctional molecule binds to the target protein and the E3 ligase enabling the transfer of ubiquitin to the target protein from the ligase provided there is a suitable acceptor on the target protein. Another method is the "molecular glue" process whereby the molecule together with the E3 ligase recruit the target protein to the E3 ligase followed by the ubiquitin transfer and degradation of the target (Chopra, R., Sadok, A., Collins, I., Drug Disc Today: Technologies, 2019, 31, 5-13.) In the case of a compound acting as a "molecular glue", the only requirement is the presence of an E3 ligase binding moiety. After binding to the E3 ligase, the ensuing moiety could recruit the protein to be degraded. The labelling of proteins with ubiquitin is implicated in the protein's turnover by the 26S proteasome.

Protein ubiquitination is a multi-step process whereby a ubiquitin protein is successively relayed between different classes of enzymes (E1, E2, E3) in order to eventually tag a cellular substrate. Initially, the C-terminal carboxylate of ubiquitin is adenylated by the E1 activating enzyme in an ATP-dependent step. Subsequently, a conserved nucleophilic cysteine residue of the E1 enzyme displaces the AMP from the ubiquitin adenylate resulting in a covalent ubiquitin thioester conjugate. The binding and ensuing adenylation of a second ubiquitin molecule promotes the recruitment of an E2 conjugating enzyme to this ternary complex. An active site Cys on the E2 subsequently facilitates the transfer of the covalently linked ubiquitin from the E1 to a Cys residue on the E2 through a trans-thioesterification reaction. Concomitantly, an E3 ligase recruits a specific downstream target protein and mediates the transfer of the ubiquitin from the E2 enzyme to the terminal substrate through either a covalent or non-covalent mechanism. Each ubiquitin is ligated to a protein through either a peptide bond with the N-terminal amino group or an isopeptide bond formed between a side chain ε-amino group of a select Lys residue on the target protein and the ubiquitin.

Deubiquitinating enzymes (DUBs) are enzymes that specifically cleave the ubiquitin protein from the substrate thereby offering additional mechanisms of regulation over the entire labeling pathway. In the current human proteome, there are eight known human E1s, about 40 E2s, over 600 E3s and over 100 DUBs. These enzymes are well described in Pavia, S. et al., *J. Med. Chem.* 2018 61(2), 405-421.

The E3 ligases originate in three major classes—the RING finger and U-box E3s, the HECT E3s, and the RING/HECT-hybrid type E3s. The E3 ligases are localized in various cell organelles and hence the effectiveness of the E3 ligase ligand depends at least in part on the location of the protein targeted for degradation, assuming that the full molecule is available within the appropriate location in the cell. In addition, for every combination of the target ligand and the ubiquitin recruiting ligand, the linker length and conformational flexibility also contributes to the effectiveness of the degradation molecule. The mechanism depends on the availability of a Lys residue on the surface of the protein close to the targeted protein ligand binding pocket. Ubiquitin binds at Lys residues and hence the "delivery" of ubiquitin for binding at the appropriate Lys influences the effectiveness of the degradation molecule. Crew et al. (US20170327469A1, US20180099940A1) are progressing a proposed treatment for castration-resistant prostate cancer based on bifunctional molecules coupling various E3 ligases to AR antagonists binding at the AR LBD site. Our approach is different in that we do not target the LBD site but the DBD site and, correspondingly, the chemical matter is quite different.

There exists a continuing need for effective treatments for diseases and conditions that are related to aberrant AR regulation or activity, for example, cancers such as prostate cancer, and Kennedy's Disease. In developing such treatments, it would be desirable to have a molecule which can simultaneously bind AR and an E3 ubiquitin ligase and which also promotes ubiquitination of AR-V7 and perhaps AR, and leads to degradation of AR-V7 and AR by the proteasome. Some compounds of this type have been described, for example, by the present Applicant in: US 2020/0239430, US 2020/0282068, WO 2020/160295 (and its equivalent U.S. Pat. No. 11,098,025), and PCT/US2021/033039 (published as WO 2021/236695), the contents of each of which are hereby incorporated by reference in their entireties.

Bi-functional compounds which function to recruit endogenous proteins to an E3 ubiquitin ligase for degradation, and methods for using same, are known. More specifically, specific proteolysis targeting chimera (PROTAC) molecules which find utility as modulators of targeted ubiquitination of a variety of polypeptides and other proteins, such as AR, which are then degraded and/or otherwise inhibited by the compounds as described herein have been described, for example, by the present Applicant in: US 2020/0239430, US 2020/0282068, and WO 2020/160295, the contents of each of which are hereby incorporated by reference in their entireties. There remains a need for improved bi-functional PROTAC compounds having superior pharmaceutical properties, such as activity, oral bioavailability, and metabolic stability.

SUMMARY OF THE INVENTION

The present disclosure provides new proteolysis targeting chimera (PROTAC) molecules which find utility as modulators of targeted ubiquitination of a variety of polypeptides and other proteins, such as AR, which are then degraded and/or otherwise inhibited by the compounds as described herein.

These PROTAC molecules comprise an E3 ubiquitin ligase binding moiety (i.e., a ligand for an E3 ubiquitin ligase) linked to a moiety that binds a target protein (i.e., a protein/polypeptide targeting ligand) such that the target protein/polypeptide is placed in proximity to the ubiquitin ligase to effect degradation (and/or inhibition) of that protein, wherein the E3LB moiety is a novel pyrrolo[3,2-b] pyridine cIAP moiety. In addition, the description provides methods for using an effective amount of the compounds described herein for the treatment or amelioration of a disease condition including cancer, e.g., prostate cancer, and Kennedy's Disease.

Suitable ligands that bind to the E3 ubiquitin ligase are known to include cereblon binders such as immunomodulatory imide drugs (IMiDs) including thalidomide, pomalidomide, and lenalidomide (Deshales, R. J., *Nature Chem Biol.* 2015 11, 634-635), and some analogs or derivatives thereof. These IMiDs act as "molecular glues" and therefore have been shown to recruit a different set of proteins for degradation (reference). Other suitable E3 ubiquitin ligase binders are the E3 CRL2$^{VHL}$ compounds, also called Von-Hippel-Lindau or VHL ligands, the cellular inhibitor of apoptosis protein (cIAP) as discussed in Shibata, N. et al., *J. Med. Chem.*, 2018 61(2), 543-575. Binders of the E3 ligase Mouse Double Minute 2 (MDM2) comprise the fourth class of E3 Ligase Binders (E3LBs) that are utilized (Skalniak, L., et al., *Expert Opin. Ther, Patents,* 2019, 29, 151-170).

The known cIAP moieties include a variety of cores, as shown in the following examples:

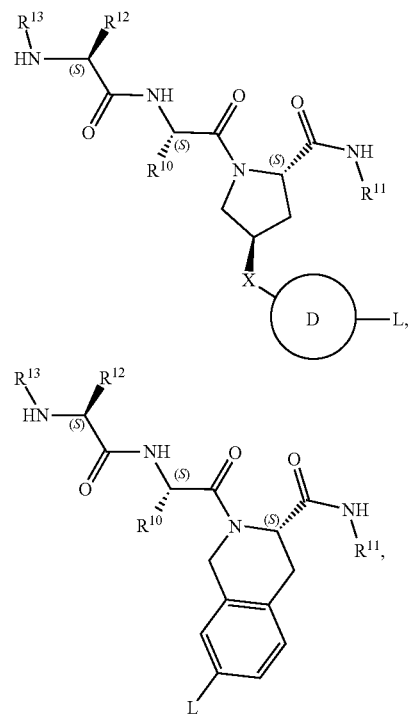

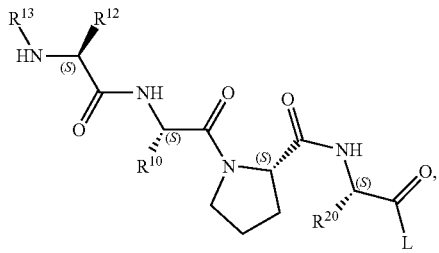

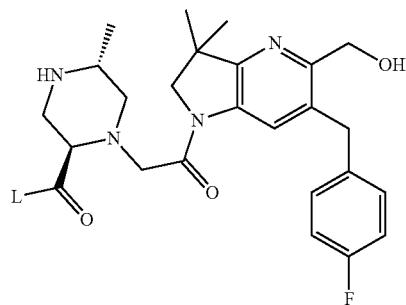

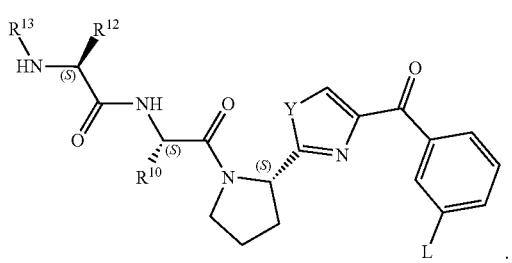

In an additional aspect, the present disclosure provides therapeutic compositions comprising an effective amount of a compound as described herein or pharmaceutically acceptable salt form thereof, and one or more pharmaceutically acceptable carriers. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation and/or inhibition of proteins of interest for the treatment or amelioration of a disease, e.g., cancer.

In another aspect, the present disclosure provides a method of ubiquitinating/degrading a target protein in a cell. In certain embodiments, the method comprises administering a bi-functional compound, or pharmaceutically acceptable salt form thereof, as described herein, such that degradation of the target protein occurs when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In another aspect, the present disclosure provides methods for treating or ameliorating a disease, disorder or symptom thereof in a subject or a patient, e.g., an animal such as a human, comprising administering to a subject in need thereof a pharmaceutical composition comprising an effective amount, e.g., a therapeutically effective amount, of a compound as described herein or pharmaceutically acceptable salt form thereof, and a pharmaceutically acceptable carrier, wherein the composition is effective for treating or ameliorating the disease or disorder or symptom thereof in the subject.

In another aspect, the present disclosure provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present disclo- In one aspect, the present disclosure provides new PROTAC compounds which function to recruit proteins, including AR-V7 and AR, for targeted ubiquitination and degradation, wherein the compounds have a structure which can be depicted as:

ARB-E3LB or ARB-L-E3LB wherein ARB is an AR binding moiety, L is a chemical linker moiety, and E3LB is a pyrrolo[3,2-b]pyridine cIAP-class ubiquitin ligase binding moiety having the following structure:

sure. The publications and other materials used herein to illuminate the background of the invention, and in particular cases, to provide additional details respecting the practice, are incorporated by reference. Where applicable or not specifically disclaimed, any one of the embodiments described herein are contemplated to be able to combine with any other one or more embodiments, even though the embodiments are described under different aspects of the disclosure.

DETAILED DESCRIPTION

The following is a detailed description provided to aid those skilled in the art in practicing the invention of the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present disclosure relates to bi-functional PROTAC compounds which facilitate E3 ubiquitin ligase-mediated ubiquitination of an androgen receptor target protein, in particular the androgen receptor of a splice variant of AR which lacks the LBD, labelled as AR-V7. Accordingly, the present description provides compounds, compositions comprising the same, and associated methods of use for ubiquitination and degradation of a chosen target protein, e.g., androgen receptor AR-V7.

In one aspect, the present disclosure provides compounds useful for regulating protein activity. The composition comprises a ubiquitin pathway protein binding moiety (preferably for an E3 ubiquitin ligase, alone or in complex with an E2 ubiquitin conjugating enzyme which is responsible for the transfer of ubiquitin to targeted proteins) according to a defined chemical structure and a protein targeting moiety which are linked or coupled together, preferably through a linker, wherein the ubiquitin pathway protein binding moiety recognizes a ubiquitin pathway protein and the targeting moiety recognizes a target protein (e.g., androgen receptor). Such compounds may be referred to herein as PROTAC compounds or PROTACs.

In one aspect, the present disclosure provides new PROTAC compounds comprising an E3 ubiquitin ligase binding moiety ("E3LB"), a moiety that binds a target protein (i.e., a protein/polypeptide targeting ligand) that is an AR binding moiety ("ARB"), and optionally a chemical linker ("L") between the E3LB and the ARB. The structure of the bi-functional compound can thus be depicted as:

ARB-E3LB or ARB-L-E3LB wherein ARB is an AR binding moiety as described herein, L is a chemical linker moiety as described herein, and E3LB is a pyrrolo[3,2-b]pyridine cIAP-class E3 ligase binding moiety having the following general structure:

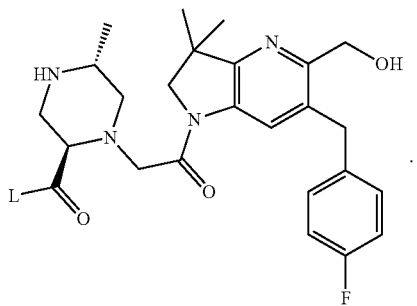

The respective positions of the ARB and E3LB moieties as well as their number as illustrated herein is provided by way of example only and is not intended to limit the compounds in any way. As would be understood by the skilled artisan, the bi-functional compounds as described herein can be synthesized such that the number and position of the respective functional moieties can be varied as desired.

It will be understood that the general structures are exemplary and the respective moieties can be arranged spatially in any desired order or configuration, e.g., ARB-L-E3LB, and E3LB-L-ARB, respectively. The E3LB group and ARB group may be covalently linked to the linker group through any covalent bond which is appropriate and stable to the chemistry of the linker. It will be further understood that for all compounds described herein, one or more hydrogen atoms may be replaced with an equivalent number of deuterium atoms.

In certain embodiments, the ARB may be selected from the following structures, wherein L is the optional linker (e.g., in the formula ARB-L-E3LB):

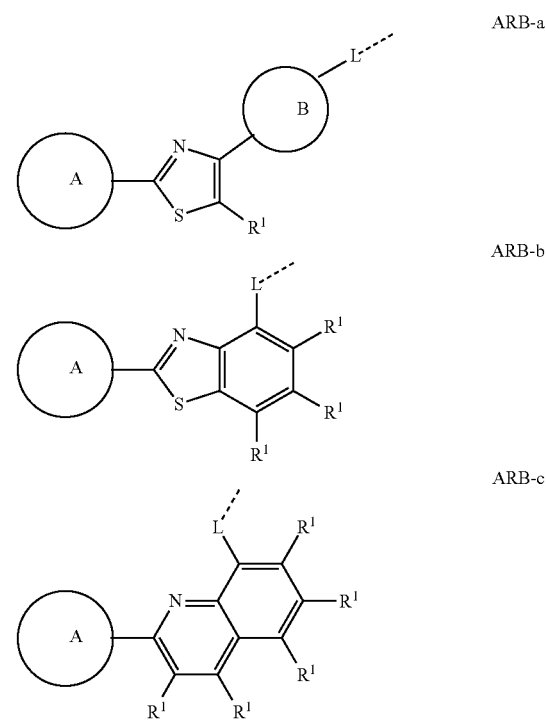

In each of ARB-a, ARB-b, and ARB-c, the following definitions apply:

L is defined as provided hereinbelow;

A is an aryl, heteroaryl, $C_{3-7}$ cycloalkyl, or 3-10 membered heterocycloalkyl ring (e.g., with 1-4 heteroatoms, such as morpholine), each of which is optionally substituted by one or more groups selected from halo (e.g., fluoro), hydroxy, nitro, cyano, $C_{1-6}$ alkyl (e.g., methyl), $C_{2-6}$ alkenyl (e.g., vinyl), or $C_{2-6}$ alkynyl (e.g., ethynyl), $NR^2R^3$, halo$C_{1-6}$ alkyl (e.g., $CH_2F$, $CHF_2$, $CF_3$), $C_{1-6}$ alkoxy (e.g., methoxy), $C_{3-6}$ cycloalkyl (e.g., cyclopropyl), aryl, heteroaryl, and 3-6 membered heterocycloalkyl (e.g., with 1-4 heteroatoms), wherein each of said alkyl, alkenyl, alkynyl, alkoxy, cycloalkyl, aryl, heteroaryl and heterocycloalkyl are independently optionally substituted by one or more halo, hydroxy, nitro, cyano, $C_{1-6}$ alkyl (e.g., methyl), halo$C_{1-6}$ alkyl (e.g., $CH_2F$, $CHF_2$, $CF_3$), $C_{1-6}$ alkoxy (e.g., methoxy), or $C_{3-6}$ cycloalkyl (e.g., cyclopropyl);

B is an aryl or heteroaryl ring, optionally substituted by one or more groups selected from halo (e.g., fluoro), hydroxy, nitro, cyano, $C_{1-6}$ alkyl (e.g., methyl), $C_{2-6}$ alkenyl (e.g., vinyl), or $C_{2-6}$ alkynyl (e.g., ethynyl), $NR^2R^3$, halo$C_{1-6}$ alkyl (e.g., $CH_2F$, $CHF_2$, $CF_3$), $C_{1-6}$ alkoxy (e.g., methoxy), $C_{3-6}$ cycloalkyl (e.g., cyclopropyl), aryl, heteroaryl, and 3-6 membered heterocycloalkyl (e.g., with 1-4 heteroatoms), wherein each of said alkyl, alkenyl, alkynyl, alkoxy, cycloalkyl, aryl, heteroaryl and heterocycloalkyl are independently optionally substituted by one or more halo, hydroxy, nitro, cyano, $C_{1-6}$ alkyl (e.g., methyl), halo$C_{1-6}$ alkyl (e.g., $CH_2F$, $CHF_2$, $CF_3$), $C_{1-6}$ alkoxy (e.g., methoxy), or $C_{3-6}$ cycloalkyl (e.g., cyclopropyl); and each $R^1$ is independently selected from H, halo (e.g., chloro or fluoro), hydroxy, —$CONH_2$, —$CONR^2R^3$, —$SONH_2$, —$SONR^2R^3$, —$SO_2NH_2$, —$SO_2NR^2R^3$, —$NHCOC_{1-3}$ alkyl (optionally substituted by 1 or more halo), —$NR^2COC_{1-3}$ alkyl (optionally substituted by 1 or more halo), —$NR^2SO_2C_{1-3}$ alkyl (optionally substituted by 1 or more halo), —$NR^2SOC_{1-3}$ alkyl (optionally substituted by 1 or more halo), cyano, $C_{1-6}$ alkyl (e.g., methyl), $C_{2-6}$ alkenyl (e.g., vinyl), or $C_{2-6}$ alkynyl (e.g., ethynyl), $NR^2R^3$, halo$C_{1-6}$ alkyl (e.g., $CH_2F$, $CHF_2$, $CF_3$), $C_{1-6}$ alkoxy (e.g., methoxy), $C_{3-6}$ cycloalkyl (e.g., cyclopropyl), or, if applicable, taken together with an $R^1$ on an adjacent atom, together with the atoms they are attached to, form a 3-6 membered heterocycloalkyl, 3-6 membered heterocycloalkenyl, $C_{3-6}$ cycloalkyl, $C_{3-6}$ cycloalkenyl, aryl, or heteroaryl ring system, wherein each of said alkyl, alkenyl, alkynyl, alkoxy, cycloalkyl, aryl, heteroaryl and heterocycloalkyl are independently optionally substituted by one or more halo, hydroxy, nitro, cyano, $C_{1-6}$ alkyl (e.g., methyl), halo$C_{1-6}$alkyl (e.g., $CH_2F$, $CHF_2$, $CF_3$), $C_{1-6}$ alkoxy (e.g., methoxy), or $C_{3-6}$ cycloalkyl (e.g., cyclopropyl); and each $R^2$ and $R^3$ is independently selected from H, halo, $C_{1-6}$ alkyl (e.g., methyl), $C_{3-6}$ cycloalkyl (e.g., cyclopropyl), or taken together with the atom they are attached to, form a 3-8 membered ring system containing 0-2 heteroatoms, wherein said alkyl or cycloalkyl is optionally substituted with one or more halo or hydroxy.

In some embodiments, A is selected from the following:

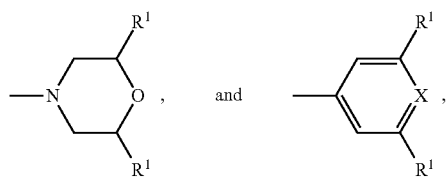

wherein $R^1$ is as described above and X is selected from —CH— or —N—.

In some embodiments, B is selected from the following:

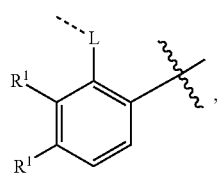

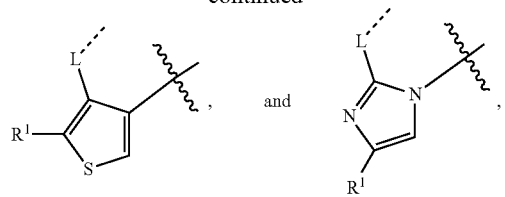

wherein L is the chemical linker and $R^1$ is as described above.

The chemical linker group (L) comprises a chemical structural unit represented by the formula -$A_q$-, in which q is an integer greater than 1; and A is independently selected from the group consisting of: a bond, $CR^{L1}R^{L2}$, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $SiR^{L1}R^{L2}$, $P(O)OR^{L1}$, $NR^{L3}C(=NCN)NR^{L4}$, $NR^{L3}C(=NCN)$, and $NR^{L3}C(=CNO_2)NR^{L4}$; wherein $R^{L1}$, $R^{L2}$, $R^{L3}$, $R^{L4}$ and $R^{L5}$ are each independently selected from the group consisting of H, halo, $C_{1-8}$ alkyl, $OC_{1-8}$ alkyl, $SC_{1-8}$ alkyl, $NHC_{1-8}$ alkyl, $N(C_{1-8}alkyl)_2$, $C_{3-11}$ cycloalkyl, aryl, heteroaryl, 3-6 membered heterocycloalkyl, $OC_{1-8}$ cycloalkyl, $SC_{1-8}$ cycloalkyl, $NHC_{1-8}$cycloalkyl, $N(C_{1-8}cycloalkyl)_2$, $N(C_{1-8}cycloalkyl)(C_{1-8}$ alkyl), OH, $NH_2$, SH, $SO_2C_{1-8}$ alkyl, $P(O)(OC_{1-8}$ alkyl)($C_{1-8}$ alkyl), $P(O)(OC_{1-8}$ alkyl)$_2$, CC—$C_{1-8}$ alkyl, CCH, CH=CH($C_{1-8}$ alkyl), $C(C_{1-8}$ alkyl)=CH($C_{1-8}$ alkyl), $C(C_{1-8}alkyl)=C(C_{1-8}alkyl)_2$, $Si(OH)_3$, $SiC(_{1-8}$ alkyl)$_3$, $Si(OH)(C_{1-8}$ alkyl)$_2$, $COC_{1-8}$ alkyl, $CO_2H$, CN, halo$C_{1-8}$ alkyl (e.g., $CF_3$, $CHF_2$, $CH_2F$), $NO_2$, $SF_5$, $SO_2NHC_{1-8}$ alkyl, $SO_2NHC_{1-8}$ alkyl, $SO_2N(C_{1-8}alkyl)_2$, $SONHC_{1-8}$ alkyl, $SON(C_{1-8}alkyl)_2$, $CONHC_{1-8}$ alkyl, $CON(C_{1-8}$ alkyl)$_2$, $N(C_{1-8}$ alkyl)$CONH(C_{1-8}$ alkyl), $N(C_{1-8}$ alkyl)$CON(C_{1-8}alkyl)_2$, $NHCONH(C_{1-8}$ alkyl), $NHCON(C_{1-8}$ alkyl)$_2$, $NHCONH_2$, $N(C_{1-8}$ alkyl)$SO_2NH(C_{1-8}$ alkyl), $N(C_{1-8}$ alkyl)$SO_2N(C_{1-8}$ alkyl)$_2$, $NHSO_2NH(C_{1-8}$ alkyl), $NHSO_2N(C_{1-8}alkyl)_2$ and $NHSO_2NH_2$.

In some embodiments, $R^{L1}$ and $R^{L2}$ each, independently can be linked to another A group to form a cycloalkyl and or heterocycloalkyl moiety that can be further substituted with 0-4 $R^{L5}$ groups.

In some embodiments, q is an integer from 1 to 30, e.g., 5 to 25, or 5 to 20, or 5 to 15, or 10 to 20, or 5 to 10, or 10 to 15, or 7 to 12.

In some embodiments, the linker moiety is preferably a flexible linker moiety, as opposed to a semi-rigid or rigid linker moiety.

It is understood that an essentially linear chain, including a linear chain with branches, such as a linear chain comprising saturated and optionally substituted —C—, —O—, —N—, and —S-atoms is highly flexible when all bonds forming the chain are sp$^2$-hybridized atoms. For example, the following are highly flexible examples of linker chains:

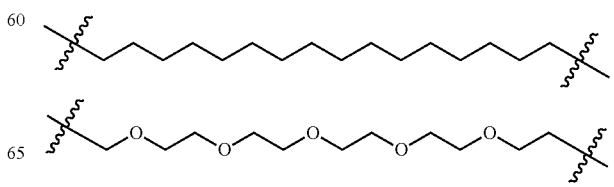

-continued

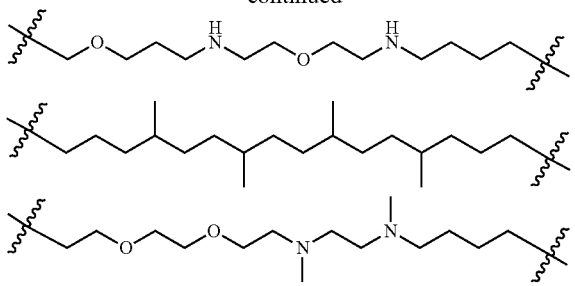

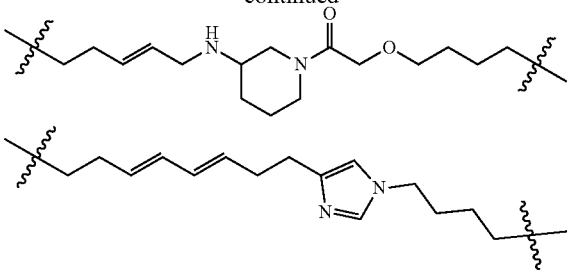

Such linker chains may lose their flexibility, becoming more rigid, by the incorporation of either rings or sp or sp$^2$-hybridized atoms, or combinations thereof. Rings (aromatic or non-aromatic) and double or triple bonds, when provided within the linker chain (not as a substituent attached to the chain) are rigid groups, which inhibit free rotation and flexibility of the linker chain L. Thus, for example, the following are examples of rigid and semi-rigid linker chains:

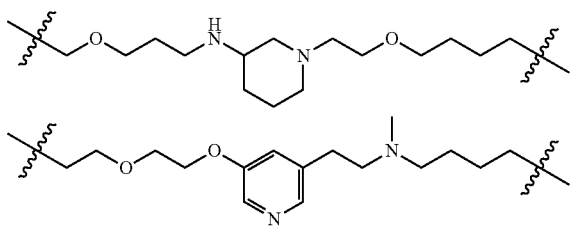

Therefore, in some embodiments, the linker moieties L of the compounds of the present disclosure comprises a structural unit represented by the formula $-A_q-$, in which q is an integer greater than 1; and L does not comprise any moieties selected from $CR^{L1}=CR^{L2}$, $C\equiv C$, $C_{3-6}$ cycloalkyl, 3-6 membered heterocycloalkyl, aryl, and heteroaryl.

In preferred embodiments, the Linker moiety "L" is a linker which consists of a chemical structural unit represented by the formula $-A_q-$, in which q is an integer greater than 1, and each A is independently selected from the group consisting of $CH_2$, O, NH, $NCH_3$, CONH, CO, $C_{3-6}$ cycloalkyl, 3-6 membered heterocycloalkyl, aryl, and heteroaryl. Preferably the Linker does not comprise any alkyl chain having more than 3 carbons (e.g., L may comprise subunits selected from —$CH_2$—, —$CH_2CH_2$—, and —$CH_2CH_2CH_2$—), and preferably the Linker comprises one or more ethyleneoxy subunits (e.g., —$CH_2CH_2O$—).

In certain embodiments, the compound is selected from the group consisting of the exemplary compounds as described below, and salts and polymorphs thereof:

Example 1

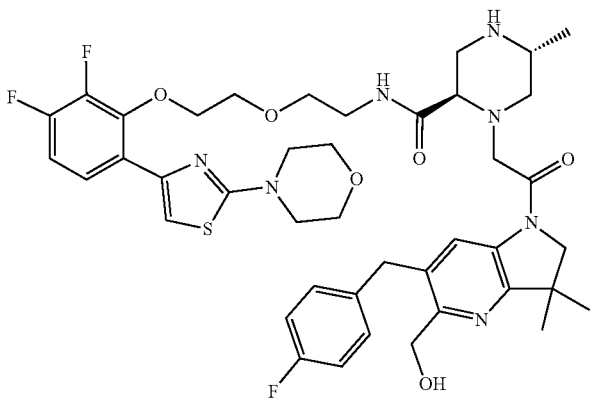 [SMILES: C[C@@H]1CN(CC(=O)N2CC(C)(C)c3nc(CO)c(Cc4ccc(F)cc4)cc32)[C@@H](C(=O)NCCOCCOc2c(-c3csc(N4CCOCC4)n3)ccc(F)c2F)CN1]

(2R,5R)-N-(2-(2-(2,3-difluoro-6-(2-morpholinothiazol-4-yl)phenoxy)ethoxy)ethyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide Example 2

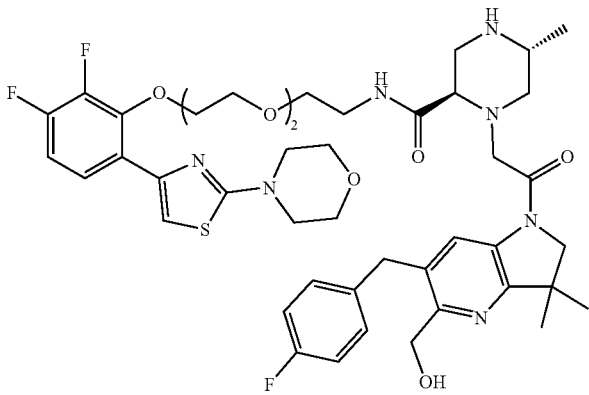

(2R,5R)-N-(2-(2-(2-(2,3-difluoro-6-(2-morpholinothiazol-4-yl)phenoxy)ethoxy)ethoxy)ethyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide -continued Example 3 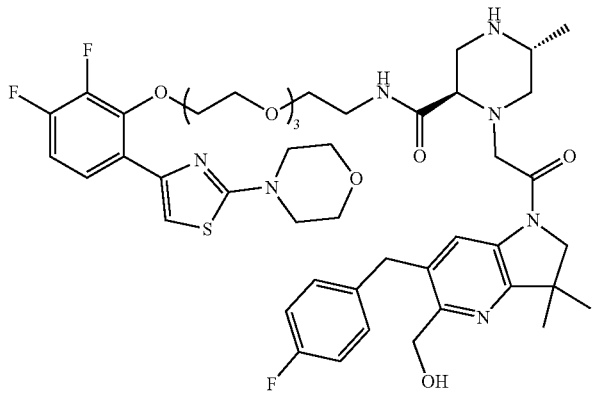 (2R,5R)-N-(2-(2-(2-(2-(2,3-difluoro-6-(2-morpholinothiazol-4-yl)phenoxy)ethoxy)ethoxy)ethoxy)ethyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide Example 4 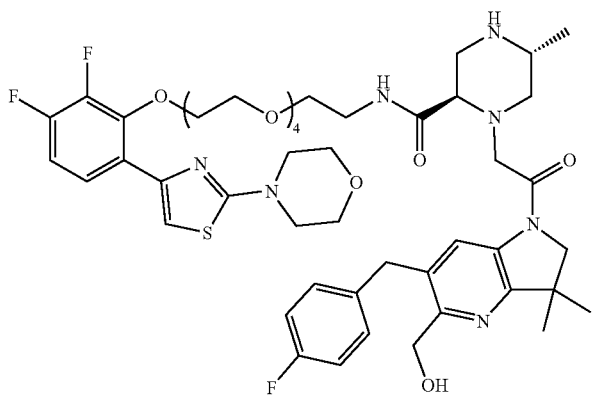 (2R,5R)-N-(14-(2,3-difluoro-6-(2-morpholinothiazol-4-yl)phenoxy)-3,6,9,12-tetraoxatetradecyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide Example 5 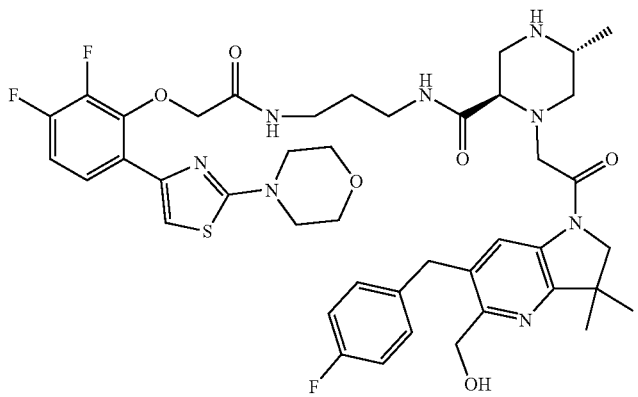 [SMILES: C[C@@H]1CN(CC(=O)N2CC(C)(C)c3nc(CO)c(Cc4ccc(F)cc4)cc32)[C@@H](C(=O)NCCCNC(=O)COc2c(-c3csc(N4CCOCC4)n3)ccc(F)c2F)CN1] (2R,5R)-N-(3-(2-(2,3-difluoro-6-(2-morpholinothiazol-4-yl)phenoxy)acetamido)propyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide Example 6 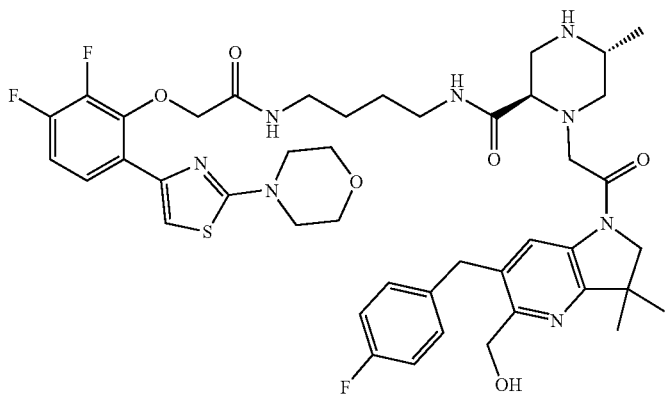 [SMILES: C[C@@H]1CN(CC(=O)N2CC(C)(C)c3nc(CO)c(Cc4ccc(F)cc4)cc32)[C@@H](C(=O)NCCCCNC(=O)COc2c(-c3csc(N4CCOCC4)n3)ccc(F)c2F)CN1] (2R,5R)-N-(4-(2-(2,3-difluoro-6-(2-morpholinothiazol-4-yl)phenoxy)acetamido)butyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide

| | | |
|---|---|---|
| Example 7 | 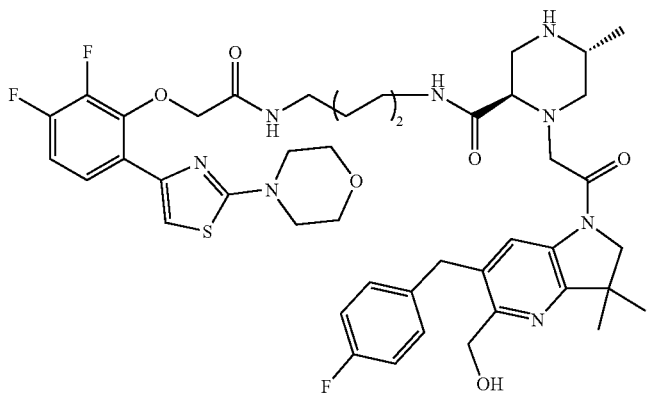 | (2R,5R)-N-(5-(2-(2,3-difluoro-6-(2-morpholinothiazol-4-yl)phenoxy)acetamido)pentyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide |
| Example 8 | 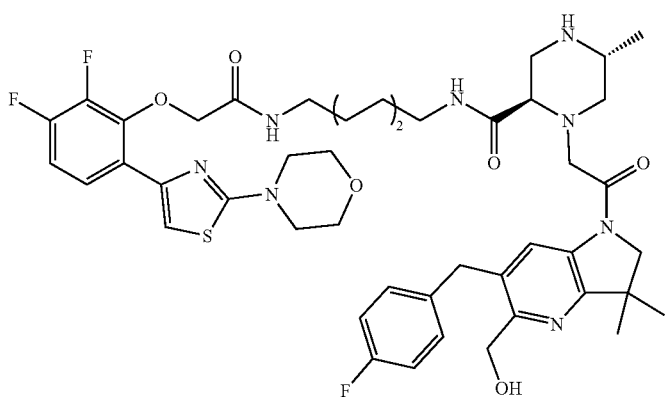 | (2R,5R)-N-(6-(2-(2,3-difluoro-6-(2-morpholinothiazol-4-yl)phenoxy)acetamido)hexyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide |
| Example 9 | 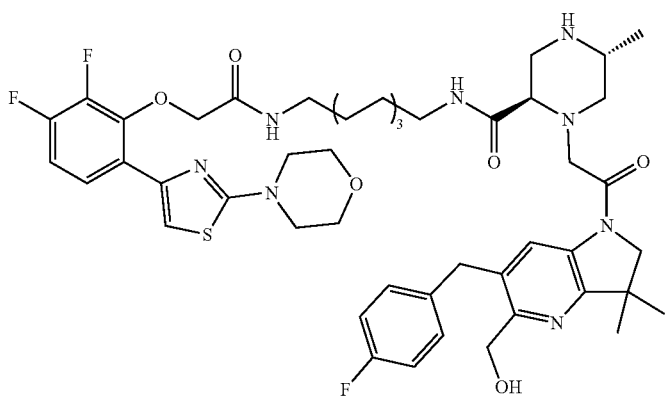 | (2R,5R)-N-(8-(2-(2,3-difluoro-6-(2-morpholinothiazol-4-yl)phenoxy)acetamido)octyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide |
| Example 10 | 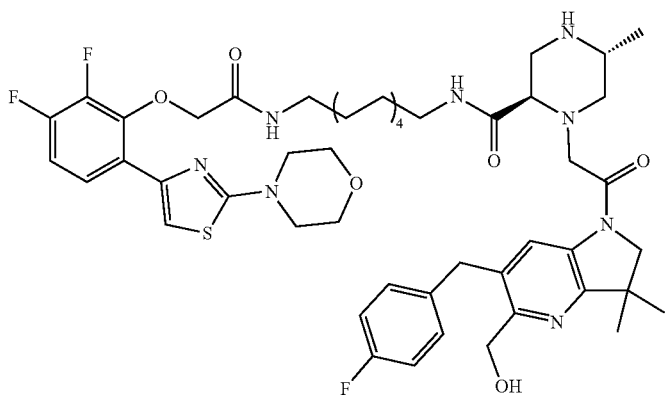 | (2R,5R)-N-(10-(2-(2,3-difluoro-6-(2-morpholinothiazol-4-yl)phenoxy)acetamido)decyl)-1-(2-(6-(4-fluorobenzyl)-5-(hydroxymethyl)-3,3-dimethyl-2,3-dihydro-1H-pyrrolo[3,2-b]pyridin-1-yl)-2-oxoethyl)-5-methylpiperazine-2-carboxamide |

In one aspect, the disclosure provides compounds of formula (I):

Such a compound is referred to as Androgen Receptor Binder-Linker-E3 Ligase Binder (I). It is understood that the terms "Androgen Receptor Binder," "Androgen Receptor Binding Moiety" and "AR Binding Moiety" refer a molecular structure which generally binds successfully to androgen receptor protein, recognizing that in different people androgen receptors will not have the identical amino acid sequence, and thus, the strength of binding may vary across different particular AR sequences.

In further embodiments of this aspect, the present disclosure provides:

1.1 A compound having a chemical structure ARB-E3LB or ARB-L-E3LB, wherein ARB is an AR binding moiety that does not bind to a ligand binding domain, E3LB is an E3 ligase binding moiety, and L is a linker coupling the AR binding moiety to the E3 ligase binding moiety, and wherein the E3LB moiety is a pyrrolo[3,2-b]pyridine cIAP-class ubiquitin ligase binding moiety having the following structure:

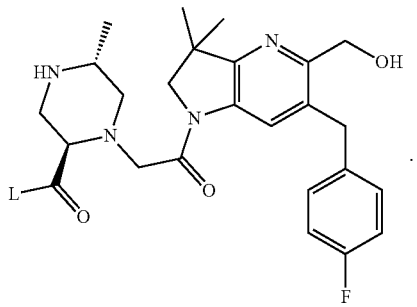

1.2 Compound 1.1, wherein the AR binding moiety binds to one more of AR splice variants V1 to V15, for example, to AR splice variant V7 (AR-V7).

1.3 Any preceding compound, wherein the AR binding moiety is selected from:

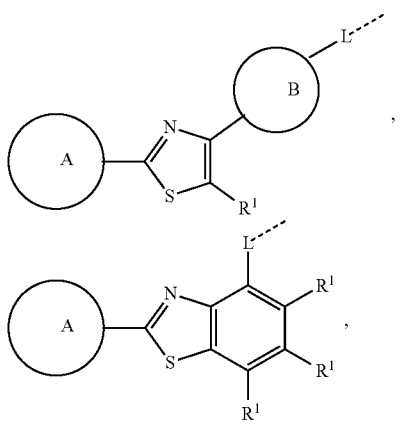

and

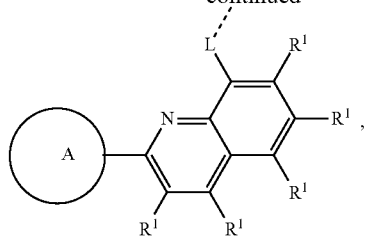

wherein:
A is an aryl (e.g., phenyl), heteroaryl (e.g., pyridyl), $C_{3-7}$ cycloalkyl, or 3-10 membered heterocycloalkyl ring (e.g., with 1-4 heteroatoms, such as morpholine), each of which is optionally substituted by one or more groups selected from halo (e.g., fluoro), hydroxy, nitro, cyano, $C_{1-6}$ alkyl (e.g., methyl), $C_{2-6}$ alkenyl (e.g., vinyl), or $C_{2-6}$ alkynyl (e.g., ethynyl), $NR^2R^3$, halo$C_{1-6}$ alkyl (e.g., $CH_2F$, $CHF_2$, $CF_3$), $C_{1-6}$ alkoxy (e.g., methoxy), $C_{3-6}$ cycloalkyl (e.g., cyclopropyl), aryl, heteroaryl, and 3-6 membered heterocycloalkyl (e.g., with 1-4 heteroatoms), wherein each of said alkyl, alkenyl, alkynyl, alkoxy, cycloalkyl, aryl, heteroaryl and heterocycloalkyl are independently optionally substituted by one or more halo, hydroxy, nitro, cyano, $C_{1-6}$ alkyl (e.g., methyl), halo$C_{1-6}$ alkyl (e.g., $CH_2F$, $CHF_2$, $CF_3$), $C_{1-6}$ alkoxy (e.g., methoxy), or $C_{3-6}$ cycloalkyl (e.g., cyclopropyl);

B is an aryl (e.g., phenyl) or heteroaryl (e.g., pyridyl or imidazolyl) ring, optionally substituted by one or more groups selected from halo (e.g., fluoro), hydroxy, nitro, cyano, $C_{1-6}$ alkyl (e.g., methyl), $C_{2-6}$ alkenyl (e.g., vinyl), or $C_{2-6}$ alkynyl (e.g., ethynyl), $NR^2R^3$, halo$C_{1-6}$ alkyl (e.g., $CH_2F$, $CHF_2$, $CF_3$), $C_{1-6}$ alkoxy (e.g., methoxy), $C_{3-6}$ cycloalkyl (e.g., cyclopropyl), aryl, heteroaryl, and 3-6 membered heterocycloalkyl (e.g., with 1-4 heteroatoms), wherein each of said alkyl, alkenyl, alkynyl, alkoxy, cycloalkyl, aryl, heteroaryl and heterocycloalkyl are independently optionally substituted by one or more halo, hydroxy, nitro, cyano, $C_{1-6}$ alkyl (e.g., methyl), halo$C_{1-6}$ alkyl (e.g., $CH_2F$, $CHF_2$, $CF_3$), $C_{1-6}$ alkoxy (e.g., methoxy), or $C_{3-6}$ cycloalkyl (e.g., cyclopropyl); and each $R^1$ is independently selected from H, halo (e.g., chloro or fluoro), hydroxy, —$CONH_2$, —$CONR^2R^3$, —$SONH_2$, —$SONR^2R^3$, —$SO_2NH_2$, —$SO_2NR^2R^3$, —$NHCOC_{1-3}$ alkyl (optionally substituted by 1 or more halo), —$NR^2COC_{1-3}$ alkyl (optionally substituted by 1 or more halo), —$NR^2SO_2C_{1-3}$ alkyl (optionally substituted by 1 or more halo), —$NR^2SOC_{1-3}$ alkyl (optionally substituted by 1 or more halo), cyano, $C_{1-6}$ alkyl (e.g., methyl), $C_{2-6}$ alkenyl (e.g., vinyl), or $C_{2-6}$ alkynyl (e.g., ethynyl), $NR^2R^3$, halo$C_{1-6}$ alkyl (e.g., $CH_2F$, $CHF_2$, $CF_3$), $C_{1-6}$ alkoxy (e.g., methoxy), $C_{3-6}$ cycloalkyl (e.g., cyclopropyl), or, if applicable, taken together with an $R^1$ on an adjacent atom, together with the atoms they are attached to, form a 3-6 membered heterocycloalkyl, 3-6 membered heterocycloalkenyl, $C_{3-6}$ cycloalkyl, $C_{3-6}$ cycloalkenyl, aryl, or heteroaryl ring system, wherein each of said alkyl, alkenyl, alkynyl, alkoxy, cycloalkyl, aryl, heteroaryl and heterocycloalkyl are independently optionally substituted by one or more halo, hydroxy, nitro, cyano, $C_{1-6}$ alkyl (e.g., methyl), halo$C_{1-6}$ alkyl (e.g., $CH_2F$, $CHF_2$, $CF_3$), $C_{1-6}$ alkoxy (e.g., methoxy), or $C_{3-6}$ cycloalkyl (e.g., cyclopropyl); and each $R^2$ and $R^3$ is independently selected from H, halo, $C_{1-6}$ alkyl (e.g., methyl), $C_{3-6}$ cycloalkyl (e.g., cyclopropyl), or taken together with the atom they are attached to, form a 3-8 membered ring system containing 0-2 heteroatoms, wherein said alkyl or cycloalkyl is optionally substituted with one or more halo or hydroxy.

1.4 Compound 1.3, wherein A is:

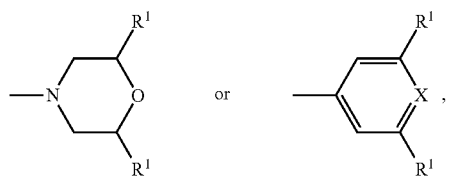

wherein X is CH or N.

1.5 Compound 1.3 or 1.4, wherein B is:

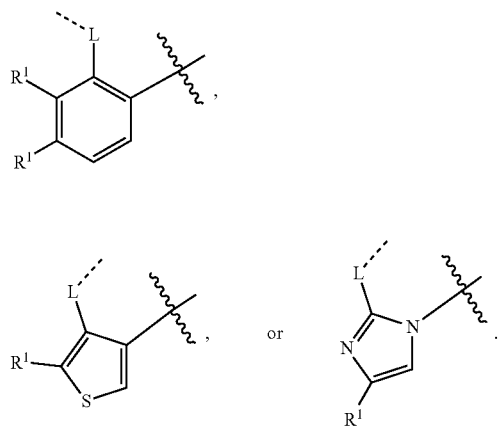

1.6 Any preceding compound, wherein the AR binding moiety is:

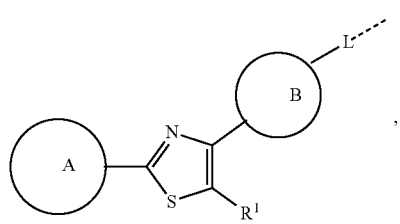

wherein:
A is a 3-10 membered heterocycloalkyl ring (e.g., with 1-4 heteroatoms, such as morpholine), B is aryl (e.g., phenyl) or heteroaryl (e.g., imidazolyl) optionally substituted by one or more halo, and $R^1$ is H, hydroxy, cyano, $NH_2$, methoxy, halo (e.g., fluoro), or $C_{1-6}$ alkyl (e.g., methyl); or the AR binding moiety is

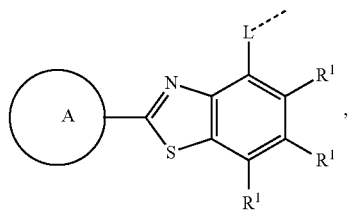

wherein:
A is a 3-10 membered heterocycloalkyl ring (e.g., with 1-4 heteroatoms, such as morpholine), and $R^1$ is H, hydroxy, cyano, $NH_2$, methoxy, halo (e.g., fluoro), or $C_{1-6}$ alkyl (e.g., methyl).

1.7 Compound 1.6, wherein A is selected from morpholinyl, piperazinyl, N-methylpiperazinyl, piperidinyl, and pyrrolidinyl.

1.8 Compound 1.6, wherein A is morpholinyl (e.g., 1-morpholinyl).

1.9 Any of Compounds 1.3 to 1.8, wherein each $R^1$ is H or halo (e.g., F, Cl or Br).

1.10 Any of Compounds 1.3 to 1.8, wherein each $R^1$ is H.

1.11 Any of Compounds 1.3 to 1.10, wherein B is phenyl optionally substituted by one or two halo (e.g., fluoro, chloro or bromo) or B is imidazolyl optionally substituted by one or two halo (e.g., fluoro, chloro or bromo).

1.12 Compound 1.11, wherein B is:

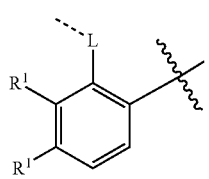

wherein each $R^1$ is independently H, F, or Cl.

1.13 Any preceding compound, wherein the AR binding moiety is selected from:

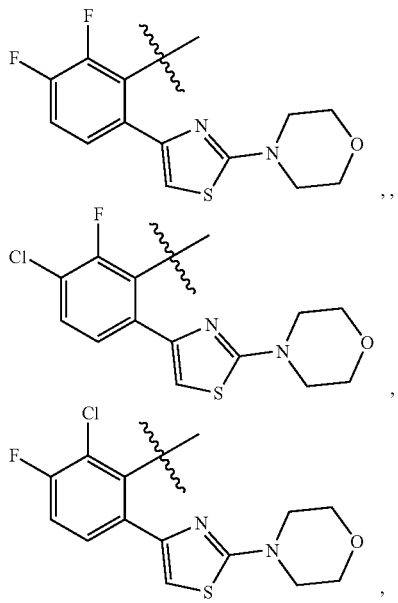

-continued

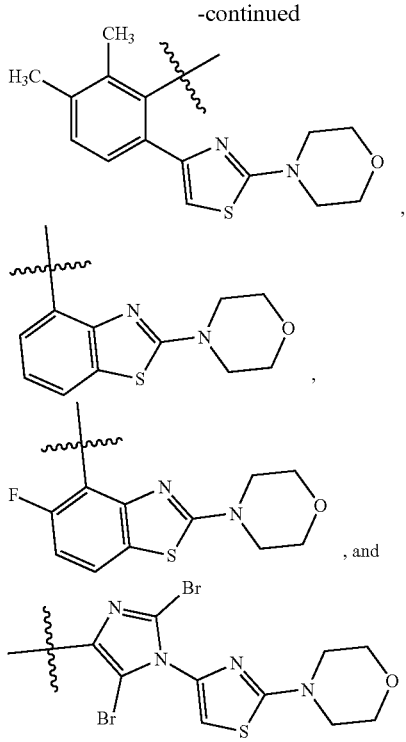

1.14 Any preceding compound, wherein the AR binding moiety is:

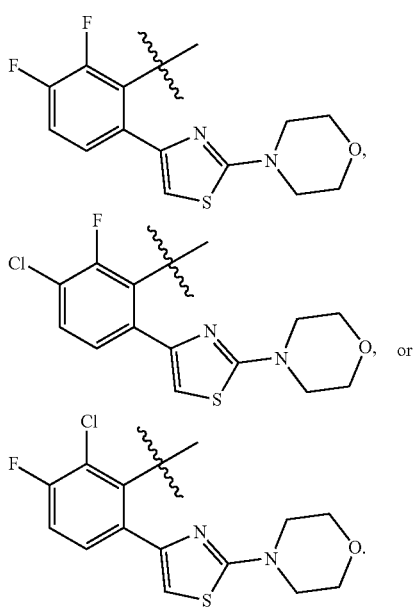

1.15 Any preceding compound, wherein the linker ("L") consists of a chemical structural unit represented by the formula -$A_q$-, in which q is an integer greater than 1, and each A is independently selected from the group consisting of: a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $SiR^{L1}R^{L2}$, $P(O)R^{L1}$, $P(O)OR^{L1}$, $NR^{L3}C(=NCN)NR^{L4}$, $NR^{L3}C(=NCN)$, and $NR^{L3}C(=CNO_2)NR^{L4}$; and wherein:

$R^{L1}$, $R^{L2}$, $R^{L3}$, $R^{L4}$ and $R^{L5}$ are each independently selected from the group consisting of H, halo, $C_{1-8}$ alkyl, $OC_{1-8}$ alkyl, $SC_{1-8}$alkyl, $NHC_{1-8}$ alkyl, $N(C_{1-8}$ alkyl$)_2$, $C_{3-11}$ cycloalkyl, aryl, heteroaryl, 3-6 membered heterocycloalkyl, $OC_{1-8}$ cycloalkyl, $SC_{1-8}$ cycloalkyl, $NHC_{1-8}$cycloalkyl, $N(C_{1-8}$cycloalkyl$)_2$, $N(C_{1-8}$ cycloalkyl)($C_{1-8}$ alkyl), OH, $NH_2$, SH, $SO_2C_{1-8}$ alkyl, $P(O)(OC_{1-8}$ alkyl)($C_{1-8}$ alkyl), $P(O)(OC_{1-8}$ alkyl$)_2$, CC—$C_{1-8}$ alkyl, CCH, CH=CH ($C_{1-8}$ alkyl), C($C_{1-8}$ alkyl)=CH($C_{1-8}$ alkyl), C($C_{1-8}$alkyl)=C($C_{1-8}$ alkyl$)_2$, $Si(OH)_3$, $SiC_{(1-8}$ alkyl$)_3$, $Si(OH)(C_{1-8}$alkyl$)_2$, $COC_{1-8}$ alkyl, $CO_2H$, CN, halo$C_{1-8}$ alkyl (e.g., $CF_3$, $CHF_2$, $CH_2F$), $NO_2$, $SF_5$, $SO_2NHC_{1-8}$ alkyl, $SO_2NHC_{1-8}$alkyl, $SO_2N(C_{1-8}$alkyl$)_2$, $SONHC_{1-8}$ alkyl, $SON(C_{1-8}$alkyl$)_2$, $CONHC_{1-8}$ alkyl, $CON(C_{1-8}$ alkyl$)_2$, $N(C_{1-8}$ alkyl)$CONH(C_{1-8}$ alkyl), $N(C_{1-8}$ alkyl)$CON(C_{1-8}$alkyl$)_2$, $NHCONH(C_{1-8}$ alkyl), $NHCON(C_{1-8}$alkyl$)_2$, $NHCONH_2$, $N(C_{1-8}$alkyl)$SO_2NH(C_{1-8}$ alkyl), $N(C_{1-8}$ alkyl)$SO_2N(C_{1-8}$alkyl$)_2$, $NHSO_2NH(C_{1-8}$ alkyl), $NHSO_2N(C_{1-8}$alkyl$)_2$ and $NHSO_2NH_2$; and wherein $R^{L1}$ and $R^{L2}$ each, independently may be linked to another A group to form a cycloalkyl and or heterocycloalkyl moiety that can be further substituted with 0-4 $R^{L5}$ groups.

1.16 Compound 1.15, wherein q is an integer from 1 to 30, e.g., 5 to 25, or 5 to 20, or 5 to 15, or 10 to 20, or 5 to 10, or 10 to 15, or 7 to 12.

1.17 Compound 1.15, wherein q is an integer from 5 to 15.

1.18 Compound 1.15, wherein q is an integer from 10 to 20.

1.19 Compound 1.15, wherein q is an integer from 5 to 10.

1.20 Any of compounds 1.15 to 1.19, wherein $R^{L1}$, $R^{L2}$, $R^{L3}$, and $R^{L5}$ are each independently selected from the group consisting of H, halo, $C_{1-8}$ alkyl, $OC_{1-8}$ alkyl, $NHC_{1-8}$ alkyl, $N(C_{1-8}$ alkyl$)_2$, $C_{3-11}$ cycloalkyl, aryl, heteroaryl, 3-6 membered heterocycloalkyl, $OC_{1-8}$ cycloalkyl, $NHC_{1-8}$cycloalkyl, $N(C_{1-8}$cycloalkyl$)_2$, $N(C_{1-8}$ cycloalkyl)($C_{1-8}$ alkyl), OH, $NH_2$, halo$C_{1-8}$ alkyl (e.g., $CF_3$, $CHF_2$, $CH_2F$), and, $CONHC_{1-8}$ alkyl.

1.21 Any of compounds 1.15 to 1.19, wherein $R^{L1}$, $R^{L2}$, $R^{L3}$, $R^{L4}$ and $R^{L5}$ are each independently selected from the group consisting of H, halo, $C_{1-8}$ alkyl, $OC_{1-8}$ alkyl, $NHC_{1-8}$ alkyl, $N(C_{1-8}$ alkyl$)_2$, $C_{3-11}$ cycloalkyl, aryl, heteroaryl, 3-6 membered heterocycloalkyl, $OC_{1-8}$cycloalkyl, and halo$C_{1-8}$ alkyl (e.g., $CF_3$, $CHF_2$, $CH_2F$).

1.22 Any of compounds 1.15 to 1.19, wherein $R^{L1}$, $R^{L2}$, $R^{L3}$, $R^{L4}$ and $R^{L5}$ are each independently selected from the group consisting of H, halo, $C_{1-8}$ alkyl (e.g., methyl), $OC_{1-8}$ alkyl (e.g., methoxy), and $C_{3-11}$ cycloalkyl (e.g., cyclopropyl).

1.23 Any of compounds 1.15 to 1.22, wherein the units A are selected from $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, and CO.

1.24 Compound 1.23, wherein the units A are selected from $CR^{L1}R^{L2}$, O, $NR^{L3}$, $SO_2NR^{L3}$, $SONR^{L3}$, $CONR^{L3}$, $NR^{L3}CONR^{L4}$, and CO.

1.25 Compound 1.24, wherein the units A are selected from $CR^{L1}R^{L2}$, O, $NR^{L3}$, $CONR^{L3}$ and CO.

1.26 Compound 1.25, wherein the units A are selected from $CH_2$, O, NH, CONH, and CO.

1.27 Any of compounds 1.15-1.26, wherein the linker is a flexible linker, e.g., the linker does not comprise any units A selected from $CR^{L1}=CR^{L2}$, C≡C, $C_{3-6}$cycloalkyl, 3-6 membered heterocycloalkyl, aryl, and heteroaryl. 1.28 Any of compounds 1.15-1.27, wherein the linker L is selected from:

[structure]

wherein n is from 1-5;

[structure]

wherein n is from 1-5;

[structure]

wherein n is from 1-5;

[structure]

wherein m is from 0-12;

[structure]

wherein m is from 0-12;

[structure]

wherein m is from 0-12;

[structure]

wherein m is from 2-4;

[structure]

wherein m is from 0-12;

[structure]

wherein m is from 0-10;

[structure]

wherein n is from 1-5;

[structure]

wherein n is from 1-5;

[structure]

wherein n is from 1-5;

[structure]

wherein m is from 0-10;

[structure]

wherein m is from 0-10;

[structure]

wherein m is from 0-10;

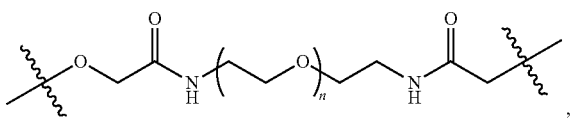,
wherein n is from 1-5;
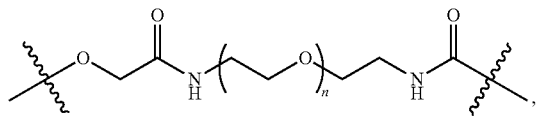,
wherein n is from 1-5;
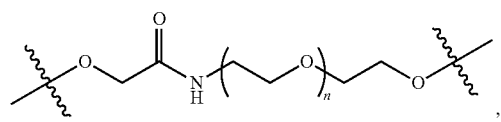,
wherein n is from 1-5;
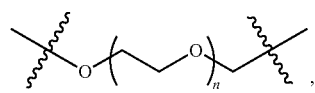,
wherein n is from 1-5;
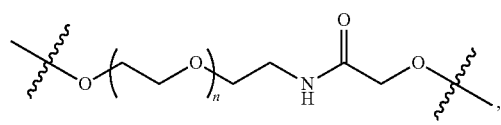,
wherein n is from 1-5;
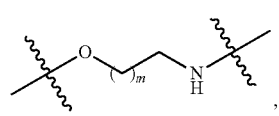,
wherein m is from 1-12;
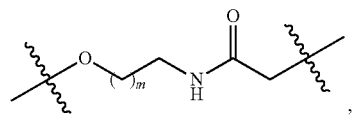,
wherein m is from 1-12;
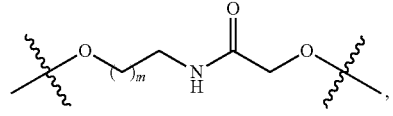,
wherein m is from 1-12; and
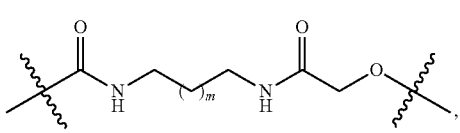,
wherein m is from 0-10.
1.29 Any of compounds 1.15-1.27, wherein the linker L is selected from:
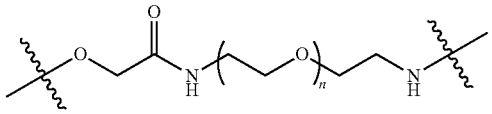,
wherein n is from 2-4;
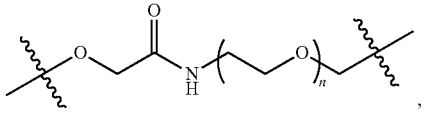,
wherein n is from 2-4;
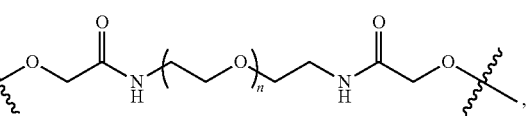,
wherein n is from 2-3;
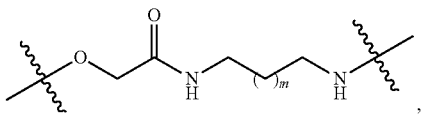,
wherein m is from 2-8;
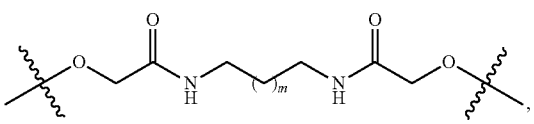,
wherein m is from 4-8;
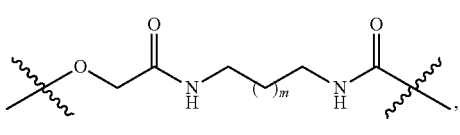,
wherein m is from 2-4;

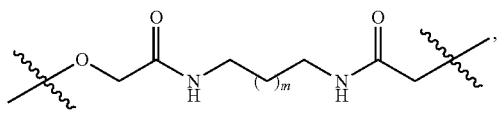

wherein m is from 2-4;

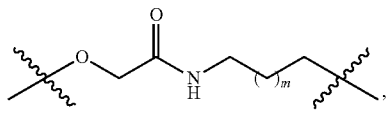

wherein m is from 1-4;

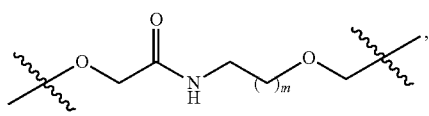

wherein m is from 1-4;

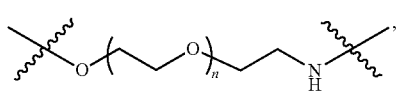

wherein n is from 2-4;

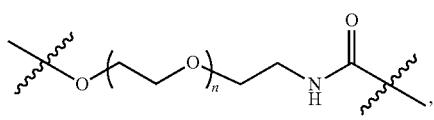

wherein n is from 1-3;

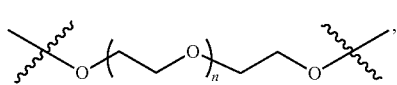

wherein n is from 1-2;

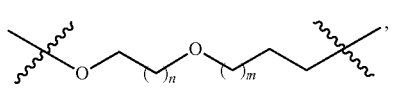

wherein n is from 1-5 and m is from 1-6;

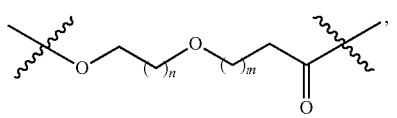

wherein n is from 1-5 and m is from 1-6;

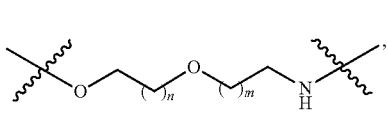

wherein n is from 1-5 and m is from 1-6;

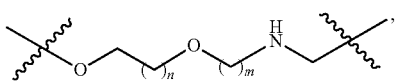

wherein n is from 1-5 and m is from 1-6;

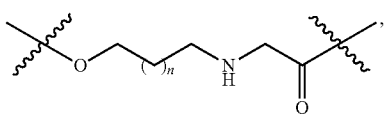

wherein n is from 0-6 (e.g., 3 or 4);

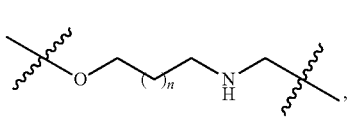

wherein n is from 0-6 (e.g., 3 or 4);

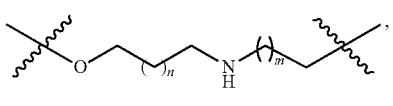

wherein n is from 0-4 (e.g., 0 or 1) and m is from 0-4 (e.g., 2 or 3);

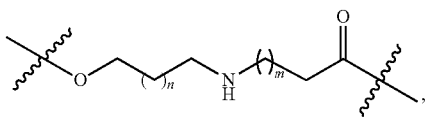

wherein n is from 0-4 (e.g., 0 or 1) and m is from 0-4 (e.g., 2 or 3);

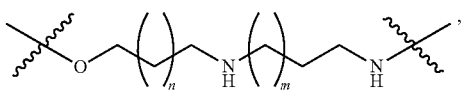

wherein n is from 0-4 (e.g., 0, 1 or 2) and m is from 0-10 (e.g., 4, 6, or 8);

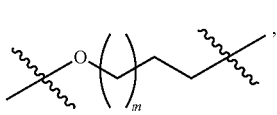

wherein m is from 4-6;

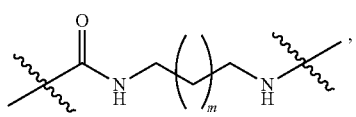

wherein m is from 2-4; and

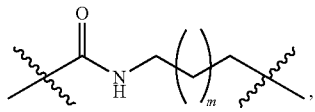

wherein m is from 2-4.

1.30 Any of compounds 1.15-1.27, wherein the linker L is selected from:

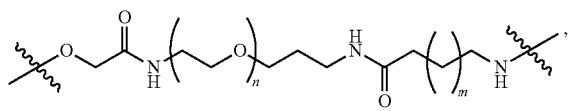

wherein n is from 0-4 (e.g., 1) and m is from 0-4 (e.g., 0);

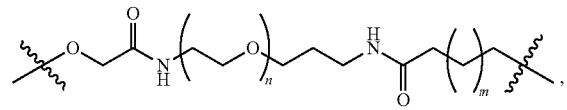

wherein n is from 0-4 (e.g., 1) and m is from 0-4 (e.g., 0);

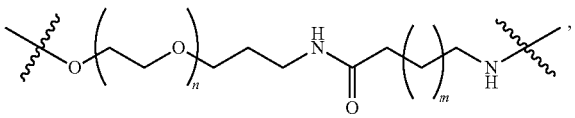

wherein n is from 0-4 (e.g., 1) and m is from 0-4 (e.g., 0);

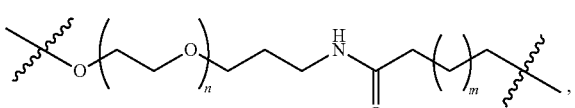

wherein n is from 0-4 (e.g., 1) and m is from 0-4 (e.g., 0);

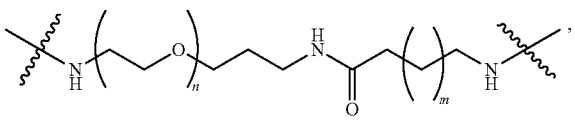

wherein n is from 0-4 (e.g., 1) and m is from 0-4 (e.g., 0);

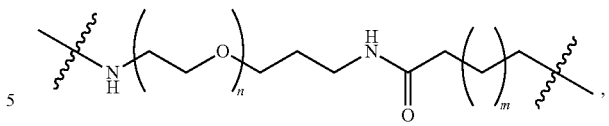

wherein n is from 0-4 (e.g., 1) and m is from 0-4 (e.g., 0);

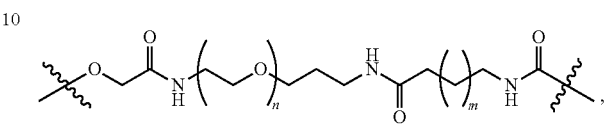

wherein n is from 0-4 (e.g., 1) and m is from 0-4 (e.g., 0);

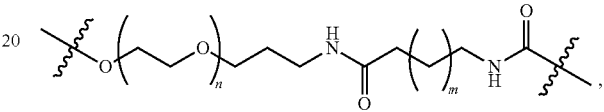

wherein n is from 0-4 (e.g., 1) and m is from 0-4 (e.g., 0);

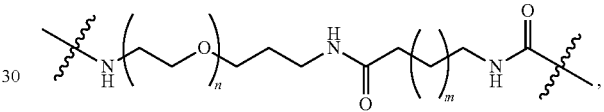

wherein n is from 0-4 (e.g., 1) and m is from 0-4 (e.g., 0);

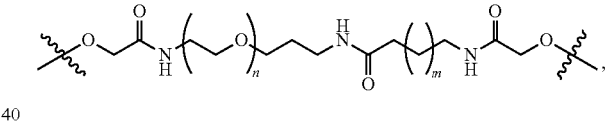

wherein n is from 0-4 (e.g., 1) and m is from 0-4 (e.g., 0);

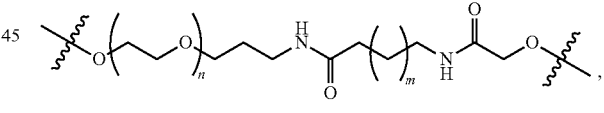

wherein n is from 0-4 (e.g., 1) and m is from 0-4 (e.g., 0);

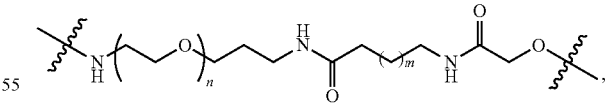

wherein n is from 0-4 (e.g., 1) and m is from 0-4 (e.g., 0);

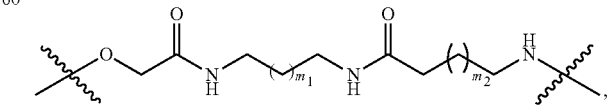

wherein $m_1$ is from 0-6 (e.g., 0 or 1) and $m_2$ is from 0-4 (e.g., 0);

[structure: chemical linker options]

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0);

wherein $m_1$ is from 0-6 (e.g., 0 or 1) and $m_2$ is from 0-4 (e.g., 0); and wherein $m_1$ is from 0-6 (e.g., 0 or 1) and $m_2$ is from 0-4 (e.g., 0).

1.31 Any of compounds 1.15-1.27, wherein the linker L is selected from:

wherein n is from 1 to 4 (e.g., 2, 3, or 4);

wherein n is from 1 to 4 (e.g., 2, 3, or 4);

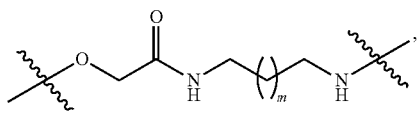
wherein m is from 2 to 8 (e.g., 4, 6, or 8);
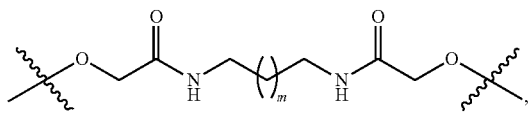
wherein m is from 2 to 8 (e.g., 4, 6, or 8);
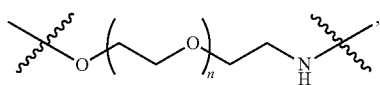
wherein n is from 1 to 4 (e.g., 2, 3, or 4);
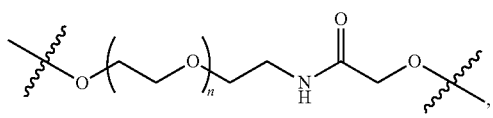
wherein n is from 1 to 4 (e.g., 2, 3, or 4);
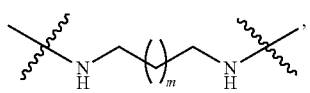
wherein m is from 2 to 8 (e.g., 4, 6, or 8);
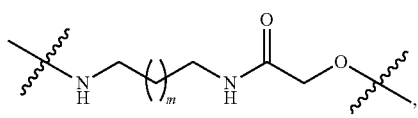
wherein m is from 2 to 8 (e.g., 4, 6, or 8);
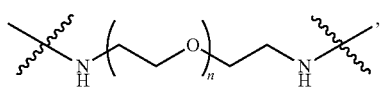
wherein n is from 1 to 4 (e.g., 2, 3, or 4); and
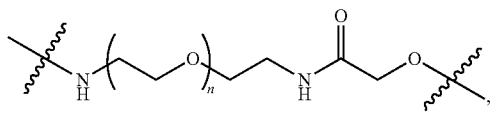
wherein n is from 1 to 4 (e.g., 2, 3, or 4).
1.32 Any of compounds 1.15-1.27, wherein the linker L is selected from:
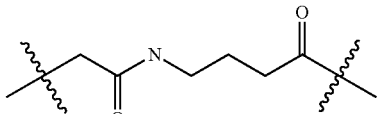
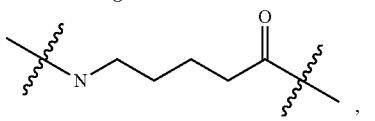
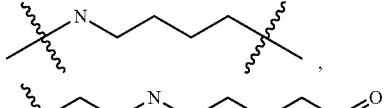
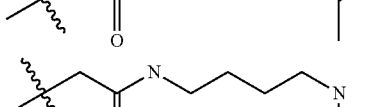
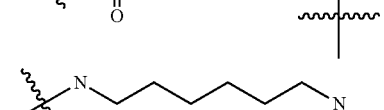
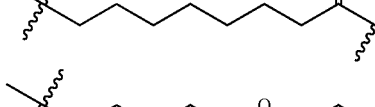
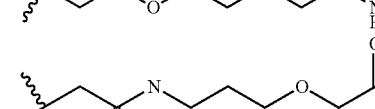
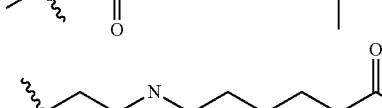
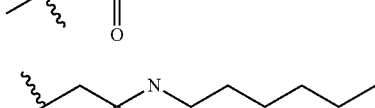
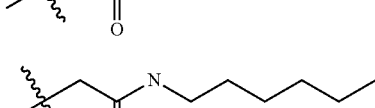
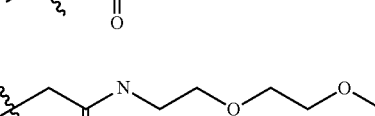
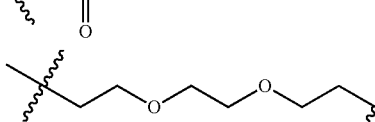
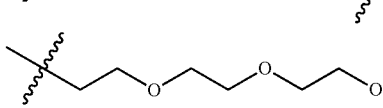

-continued

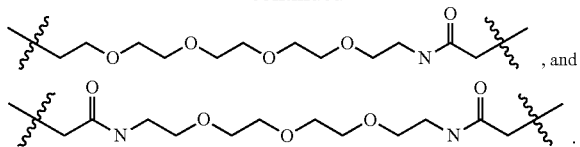, and

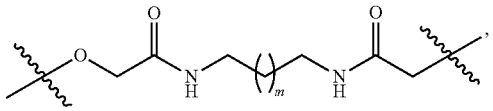

wherein m is from 2-4;

1.33 Any preceding compound, wherein the compound comprises:

the AR binding moiety

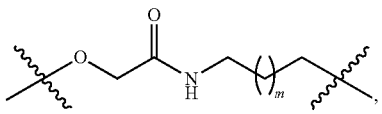

wherein m is from 0-12;

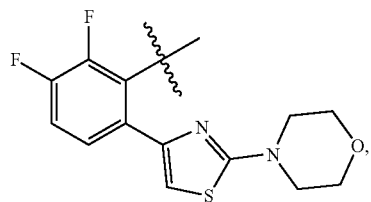

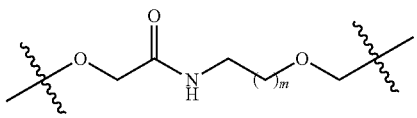

wherein m is from 0-10;

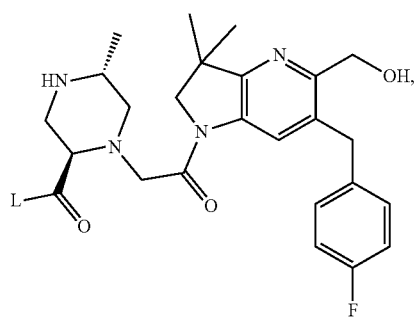

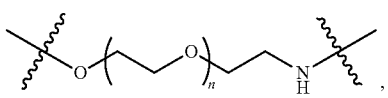

wherein n is from 1-5; and

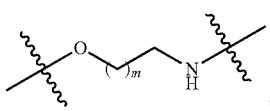

wherein m is from 1-12.

and the E3 ligase binding moiety and a linker selected from:

1.34 Compound 1.33, wherein the linker L is selected from:

wherein n is from 1-5;

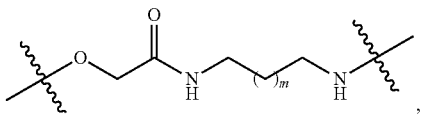

wherein m is from 0-8 (e.g., 2, 4, 6, or 8); and

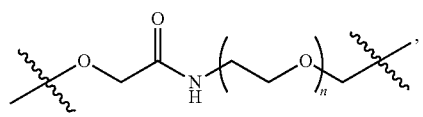

wherein n is from 1-5;

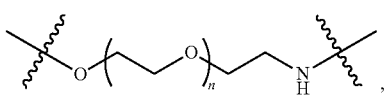

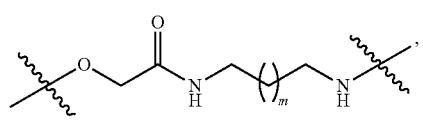

wherein n is from 1-3 (e.g., 1, 2, or 3).

1.35 Any preceding compound, wherein the compound is selected from any one or more of Examples 1 to 10 in the table above.

1.36 Any of Compounds 1.1-1.35 wherein the compound is effective in causing or promoting the degradation of the androgen receptor (AR) in a cell, or of causing or promoting apoptosis in a cell.

wherein m is from 0-12;

1.37 Compound 1.36, wherein the cell is a cancer cell (e.g., a prostate cancer cell or ovarian cancer cell, for example, castration-resistant prostate cancer (CRPC) cell).

1.38 Compound 1.36 or 1.37, wherein the cell overexpresses the AR or expresses a mutated AR, such as an AR having a truncated ligand binding domain or absent ligand binding domain.

1.39 Compound 1.38, wherein the mutant AR is any AR-V1 to AR-V15 splice variant, e.g., the AR-V7 splice variant.

1.40 A pharmaceutical composition comprising any of Compounds 1.1-1.39 (e.g., an effective amount of any of Compounds 1.1-1.39), and a pharmaceutically acceptable carrier, additive and/or excipient.

1.41 Pharmaceutical Composition 1.40, further comprising at least one additional anticancer agent.

1.42 Any of Compounds 1.1-1.39, or pharmaceutical composition 1.40 or 1.41, for use in the treatment of a disease state or condition in a patient wherein dysregulated protein activity is responsible for said disease or condition.

1.43 Use of any of Compounds 1.1-1.39, or pharmaceutical composition 1.40 or 1.41, in the treatment of a disease state or condition in a patient wherein dysregulated protein activity is responsible for said disease or condition.

1.44 A Method of treating a disease state or condition in a patient wherein dysregulated protein activity is responsible for said disease or condition, said method comprising administering an effective amount of any of Compounds 1.1-1.39, or pharmaceutical composition 1.40 or 1.41, to a patient in need thereof.

1.45 Any of the Uses or Methods according to 1.42 to 1.44, wherein the disease or condition is a cancer.

1.46 Any of the Uses or Methods according to 1.42 to 1.45, wherein the disease or condition is a cancer identified as having a mutation resulting, or expected to result in, overexpression of the androgen receptor.

1.47 Use or Method 1.46, wherein the cell expresses a mutated androgen receptor, e.g., one in which there is a mutation in the ligand binding domain of the AR.

1.48 Use or Method 1.47, wherein the ligand binding domain of the AR is truncated or absent.

1.49 Any of Uses or Methods 1.44-1.48, wherein the cell expresses or overexpresses any AR-V1 to AR-V15 splice variant, e.g., the AR-V7 splice variant.

1.50 Any of the uses or methods according to 1.48 to 1.49, wherein the cancer is a prostate cancer or ovarian cancer.

1.51 Use or Method 1.50, wherein the cancer is a prostate cancer, for example, castration-resistant prostate cancer (CRPC).

1.52 Any of the uses or methods according to 1.42 to 1.51, wherein the disease or condition is not responsive to, or no longer responsive to, treatment with an androgen receptor antagonist (e.g., abiraterone, apalutamide, enzalutamide, or darolutamide).

1.53 Any of Compounds 1.1-1.39, or pharmaceutical composition 1.40 or 1.41, for use in the degradation of an androgen receptor in a cell, e.g., a mutated AR such as any AR-V1 to AR-V15 splice variant, e.g., the AR-V7 splice variant.

1.54 Use of any of Compounds 1.1-1.39, or pharmaceutical composition 1.40 or 1.41, in the degradation of an androgen receptor (AR) in a cell, e.g., a mutated AR such as any AR-V1 to AR-V15 splice variant, e.g., the AR-V7 splice variant.

1.55 A Method of degrading an androgen receptor in a cell, e.g., a mutated AR such as any AR-V1 to AR-V15 splice variant, e.g., the AR-V7 splice variant, said method comprising administering an effective amount of any of Compounds 1.1-1.39, or pharmaceutical composition 1.40 or 1.41, to such cell.

1.56 Any of Uses or Methods 1.53-1.55, wherein the cell is a cancer cell (e.g., a prostate cancer cell or ovarian cancer cell, for example, castration-resistant prostate cancer (CRPC) cell).

1.57 Any of Uses or Methods 1.53-1.56, wherein the cell overexpresses the AR or expresses a mutated AR, such as an AR having a truncated ligand binding domain or absent ligand binding domain.

1.58 Use or Method 1.57, wherein the mutant AR is any AR-V1 to AR-V15 splice variant, e.g., the AR-V7 splice variant.

1.59 Any of Uses or Methods 1.53-1.58, wherein the AR is resistant to inhibition by an AR antagonist (e.g., abiraterone, apalutamide, enzalutamide, or darolutamide).

1.60 Any of Compounds 1.1-1.39, or pharmaceutical composition 1.40 or 1.41, for use in inducing apoptosis in a cell, e.g., a cancer cell.

1.61 Use of any of Compounds 1.1-1.39, or pharmaceutical composition 1.40 or 1.41, in the induction of apoptosis in a cell, e.g., a cancer cell.

1.62 A Method of inducing apoptosis in a cell, e.g., a cancer cell, said method comprising administering an effective amount of any of Compounds 1.1-1.39, or pharmaceutical composition 1.40 or 1.41, to such cell.

1.63 Any of Uses or Methods 1.60-1.62, wherein the cell is a prostate cancer cell or ovarian cancer cell (for example, castration-resistant prostate cancer (CRPC) cell).

1.64 Any of Uses or Methods 1.60-1.63, wherein the cell overexpresses the androgen receptor (AR) or expresses a mutated AR, such as an AR having a truncated ligand binding domain or absent ligand binding domain.

1.65 Use or Method 1.64, wherein the mutant AR is any AR-V1 to AR-V15 splice variant, e.g., the AR-V7 splice variant.

1.66 Any of Uses or Methods 1.53-1.65, wherein the cell is from a patient suffering from or diagnosed with cancer.

1.67 Any of Uses or Methods 1.53-1.65, wherein the cell is in a patient suffering from or diagnosed with cancer.

Definitions

Unless otherwise defined, all technical and scientific terms used herein have the same meaning as commonly understood by one of ordinary skill in the art to which this disclosure belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present disclosure. In instances where a term is not specifically defined herein, that term is given an art-recognized meaning by those of ordinary skill applying that term in context to its use in describing the present invention.

The articles "a" and "an" as used herein and in the claims are used herein to refer to one or to more than one (i.e., to at least one) of the grammatical object of the article unless the context clearly indicates otherwise. By way of example, "an element" means one element or more than one element.

The phrase "and/or" as used herein and in the claims should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the term "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "about" and the like, as used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the term "about" is normally used to encompass values within the standard deviation or standard error.

In the claims, as well as in the specification, all transitional phrases such as "comprising," "including," "carrying," "having," "containing," "involving," "holding," "composed of," and the like are to be understood to be open-ended, i.e., to mean "including without limitation". Only the transitional phrases "consisting of" and "consisting essentially of" shall be closed or semi-closed transitional phrases, respectively, as set forth in the United States Patent Office Manual of Patent Examining Procedures, Section 2111.03.

It should also be understood, that although various compounds, compositions, and methods are described in "open" terms of "comprising," "including," or "having" various components or steps (interpreted as meaning "including without limitation"), the compounds, compositions, methods, and devices can also "consist essentially of" or "consist of" the various components and steps, and such terminology should be interpreted as defining essentially closed-member groups. This paragraph is not meant in any way to limit the meaning of "comprising," "having," or "including" (and other verb forms thereof) which are to be interpreted as open-ended phrases meaning "including without limitation" consistent with patent law and custom. The intent of this paragraph is merely to indicate that the closed-member groups defined by the "consisting of" or "consisting essentially of" language are lesser included groups within the open-ended descriptions and to provide support for claims employing the "consisting of" or "consisting essentially of" language.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" can refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "effective" can mean, but is in no way limited to, that amount/dose of the active pharmaceutical ingredient, which, when used in the context of its intended use, effectuates or is sufficient to prevent, inhibit the occurrence, ameliorate, delay or treat (alleviate a symptom to some extent, preferably all) the symptoms of a condition, disorder or disease state in a subject in need of such treatment or receiving such treatment. The term effective subsumes all other effective amount or effective concentration terms, e.g., "effective amount/dose," "pharmaceutically effective amount/dose" or "therapeutically effective amount/dose," which are otherwise described or used in the present application.

The effective amount depends on the type and severity of disease, the composition used, the route of administration, the type of mammal being treated, the physical characteristics of the specific mammal under consideration, concurrent medication, and other factors which those skilled in the medical arts will recognize. The exact amount can be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington, *The Science and Practice of Pharmacy*, 20th Edition, 2003, Gennaro, Ed., Lippincott, Williams & Wilkins).

The term "pharmacological composition," "therapeutic composition," "therapeutic formulation" or "pharmaceutically acceptable formulation" can mean, but is in no way limited to, a composition or formulation that allows for the effective distribution of an agent provided by the present disclosure, which is in a form suitable for administration to the physical location most suitable for their desired activity, e.g., systemic administration.

The term "pharmaceutically acceptable" can mean, but is in no way limited to, entities and compositions that do not produce an adverse, allergic or other untoward reaction when administered to a patient or subject.

The term "pharmaceutically acceptable carrier" can mean, but is in no way limited to, any and all solvents, dispersion media, coatings, antibacterial and antifungal agents, isotonic and absorption delaying agents, and the like, compatible with pharmaceutical administration to a patient or subject. Suitable carriers are described in the most recent edition of Remington's *Pharmaceutical Sciences*, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular.

The rate of entry of a drug into the circulation has been shown to be a function of molecular weight or size. The use of a liposome or other drug carrier comprising the compounds of the instant disclosure can potentially localize the drug, for example, in certain tissue types, such as the tissues of the reticular endothelial system (RES). A liposome formulation which can facilitate the association of drug with the surface of cells, such as, lymphocytes and macrophages is also useful.

The terms "patient" and "subject" are used throughout the specification to describe a cell, tissue, or animal, preferably a mammal, e.g., a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "compound," as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. The term also refers to any specific chemical compound in which one or more atoms have been replaced with one or more different isotopes of the same element. It is noted that in describing the present compounds, numerous substituents and variables associated with same, among others, are described.

It is understood by those of ordinary skill that molecules which are described herein are stable compounds as generally described hereunder. When the bond is shown, both a double bond and single bond are represented or understood within the context of the compound shown and well-known rules for valence interactions.

As used herein, "derivatives" can mean compositions formed from the native compounds either directly, by modification, or by partial substitution. As used herein, "analogs" can mean compositions that have a structure similar to, but not identical to, the native compound.

The term "ubiquitin ligase" refers to a family of proteins that facilitate the transfer of ubiquitin to a specific substrate protein, targeting the substrate protein for degradation. For example, cereblon is an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase may be involved in polyubiquitination such that a second ubiquitin may be attached to the first; a third may be attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins may not be targeted to the proteasome for degradation, but may instead be altered in their cellular location or function, for example, via binding other proteins that have domains capable of binding ubiquitin. Further, different lysine residues on ubiquitin can be targeted by an E3 to make chains. The most common lysine is Lys48 on the ubiquitin chain. This is the lysine used to make polyubiquitin, which is recognized by the proteasome.

As used herein, the terms "halo" or "halogen" means fluoro (F), chloro (Cl), bromo (Br) or iodo (I).

As used herein, the term "alkyl" means a linear or branched fully saturated hydrocarbon radical or group, preferably a $C_1$-$C_{10}$, more preferably a $C_1$-$C_6$, alternatively a $C_1$-$C_3$ group, which may be optionally substituted. Examples of alkyl groups include, but are not limited to, methyl, ethyl, propyl, isopropyl, n-butyl, sec-butyl, t-butyl, n-pentyl, isopentyl, neopentyl, n-hexyl, n-heptyl, n-octyl, n-nonyl, n-decyl, or any other acyclic hydrocarbon group having the general formula —$C_nH_{2n+1}$.

As used herein, the term "alkenyl" refers to a linear or branched unsaturated hydrocarbon radical group having at least one carbon-carbon double bond, preferably a $C_2$-$C_{10}$, more preferably a $C_2$-$C_6$, which may be optionally substituted. Preferably, said group is mono-unsaturated (having a single carbon-carbon double bond). Examples of alkenyl groups include, but are not limited to, vinyl and allyl, or any other hydrocarbon acyclic group having the general formula —$C_nH_{2n-1}$.

As used herein, the term "alkynyl" refers to a linear or branched hydrocarbon radical group having at least one carbon-carbon triple bond, preferably a $C_2$-$C_{10}$, more preferably a $C_2$-$C_6$, which may be optionally substituted. Preferably, said group is mono-unsaturated (having a single triple bond). Examples of alkynyl groups include, but are not limited to, ethynyl and propargyl, or any other acyclic group having at least one triple bond and the general formula —$C_nH_{2n-3}$. As used herein, hydrocarbon radicals having both a double bond and a triple bond are considered alkynyl radicals.

As used herein, the term "alkylene" refers to a —$(CH_2)_n$— group (wherein n is an integer generally from 1-10, such as 1-6), which may be optionally substituted. When substituted, the alkylene group preferably is substituted on one or more of the methylene groups with a $C_1$-$C_6$ alkyl group (including a cyclopropyl group or a t-butyl group), more preferably a methyl group, but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, (3-alanine, arginine, asparagine, aspartic acid, cysteine, cystine, glutamic acid, glutamine, glycine, phenylalanine, histidine, isoleucine, lysine, leucine, methionine, praline, serine, threonine, valine, tryptophan, or tyrosine.

As used herein, a range of carbon atoms which includes Co means that carbon is absent and is replaced with H (or deuterium). Thus, a range of carbon atoms which is $C_0$-$C_6$ includes carbons atoms of 1, 2, 3, 4, 5 and 6 and for Co, H (or deuterium) stands in place of carbon.

As used herein, the term "unsubstituted" means substituted only with hydrogen atoms.

As used herein, it is understood that each of the independent groups, moieties, or units (these terms are synonymous) "A" which form the linker moiety L are bivalent groups having two "open" valences for attachment to other atoms. It is understood that the unit "CO" refers to a carbonyl group, —C(=O)—, and thus any reference to "CO" as a bivalent radical is understood as indicated the attachment of two atoms to the carbon atom of the "CO" unit. Similarly, when used in combination with other hetero atoms, such as in the term "$NR^{L3}CONR^{L4}$" it is understood that the carbonyl carbon atom is attached to each of the two nitrogen atoms, each of which has a single attached R-group ($R^{L3}$ or $R^{L4}$), and wherein the entire bivalent radical "$NR^{L3}CONR^{L4}$" is attached two additional atoms at each of the nitrogen atoms. Similarly, the term "$NR^{L3}SO_2NR^{L4}$" refers to a bivalent radical having attachment point on each nitrogen atom with the two nitrogen atoms bridge by the sulfur atom of a sulfonyl group, —S(O)(O)— or —S($O_2$)—. It is further understood that the terms "CO" and "—C(O)—" are interchangeable. More generally, in complex functional groups such as $SiR^{L1}R^{L2}$, $P(O)R^{L1}$, and $P(O)OR^{L1}$, it is understood that the connections of these bivalent groups to other atoms is on the central atom, i.e., the silicon atom or the phosphorus atom, and that the R-groups or OR-groups are also attached to the central atom. It is further understood that in the bivalent radicals SO, and $SO_2$, the oxygen atom or atoms are bonded to the sulfur atom, and the open valences are both on the sulfur atom in each instance.

As used herein, the term "substituted" or "optionally substituted" means that one or more hydrogen atoms of a group or radical is independently (i.e., where more than a single substitution occurs, each substituent is independent of another substituent) replaced by one or more non-hydrogen substituents, up to the maximum permissible number of substituents for the chemical structure, substructure, group or radical, for example, up to five substituents, preferably up to three substituents, often 1 or 2 substituents on a moiety. Substituents may themselves be further substituted. Optional substituents, unless indicated otherwise, include hydroxy (—OH), thiol (—SH), carboxy (—COOH), cyano (—CN), nitro (—$NO_2$), halogen (preferably, F or Cl), $C_1$-$C_{20}$alkyl (e.g., $C_1$-$C_{10}$alkyl, $C_1$-$C_6$alkyl), $C_2$-$C_{20}$alkenyl (e.g., $C_2$-$C_{10}$alkenyl, $C_2$-$C_6$alkenyl), $C_2$-$C_{20}$alkynyl (e.g., $C_2$-$C_{10}$alkynyl, $C_2$-$C_6$alkynyl), aryl (e.g., phenyl, napthyl), heteroaryl (e.g., 5- to 10-membered ring heteroaryls, such as azoles, diazoles, triazoles, pyridine, diazines, triazines, and benzo-fused derivatives thereof), 5-10 membered heterocycloalkyl (containing at least one heteroatom N, S, or O), $C_1$-$C_{20}$alkoxy (e.g., $C_1$-$C_{20}$alkoxy, $C_1$-$C_6$alkoxy), $C_3$-$C_{20}$cycloalkyl (e.g., $C_3$-$C_{10}$cycloalkyl, $C_3$-$C_6$cycloalkyl), $C_3$-$C_{20}$cycloalkoxy (e.g., $C_3$-$C_{10}$cycloalkoxy, $C_3$-$C_6$cycloalkoxy), aryloxy (e.g., phenoxy), thioether (thio$C_1$-$C_6$alkyl or aryl), keto, acyl (preferably, $C_1$-$C_6$ acyl), ester or thioester (preferably, $C_1$-$C_6$ alkyl or aryl; including alkylene ester, such that attachment is on the alkylene group, rather than at the ester function which is preferably substituted with a $C_1$-$C_6$ alkyl or aryl group), amine (including amino (—$NH_2$), mono-$C_1$-$C_6$alkylamino, di-$C_1$-$C_6$alkylamino, five- or six-membered N-containing heterocycloalkyl), carbamate or urethane (such as optionally substituted N($C_0$-$C_6$ alkyl)C(O)(O$C_1$-$C_6$ alkyl) group), hydrazine or hydrazide, amido (N—C(O), preferably substituted with one or two $C_1$-$C_6$ alkyl groups; including a carboxamido which is optionally substituted with one or two $C_1$-$C_6$ alkyl groups), sulfone ($SO_2$), sulfoxide (S(O)), sulfonamide, alkanol (preferably, $C_1$-$C_6$ alkyl or aryl, such as $(CH_2)_nOH$), or alkanoic acid (preferably, $C_1$-$C_6$ alkyl or aryl, such as $(CH_2)_nCOOH$), wherein n is an integer from 1-10, e.g., 1-6. Substituents according to the present invention may also include $SiR_1R_2R_3$ groups wherein each of $R_1$ and $R_2$ is as otherwise described herein, and $R_3$ is H or a $C_1$-$C_6$ alkyl group, preferably $R_1$, $R_2$, $R_3$ in this context is a $C_1$-$C_3$ alkyl group (including an isopropyl or t-butyl group). Additional optional substituents include: NHC(O)NH, $(CH_2)_nSH$, $(CH_2)_nO(C_1$-$C_6$ alkyl), $(CH_2)_nC(O)(C_1$-$C_6$ alkyl), $(CH_2)_nOC(O)(C_1$-$C_6$alkyl), $(CH_2)_nC(O)O(C_1$-$C_6$ alkyl), $(CH_2)_nNHC(O)R_1$, $(CH_2)_nC(O)NR_1R_2$, $(OCH_2)_nOH$, $(CH_2O)_nCOOH$, $C_1$-$C_6$ alkyl, $(OCH_2)_nO(C_1$-$C_6$ alkyl), $(CH_2O)_nC(O)(C_1$-$C_6$ alkyl), $(OCH_2)_nNHC(O)R_1$, $(CH_2O)_nC(O)NR_1R_2$, $S(O)_2R_s$, and $S(O)R_s$ ($R_s$ is $C_1$-$C_6$ alkyl or a $(CH_2)_mNR_1R_2$ group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or, alternatively, an optionally substituted —$(OCH_2)_m$—, —$(OCH_2CH_2)_m$— or —$(CH_2CH_2O)_m$— group, which may be substituted with any one or more of the above-described substituents, wherein m is an integer from 1 to 20, e.g., 1 to 10 or 1 to 6. Alkylene groups —$(CH_2)_m$— or —$(CH_2)_n$— groups or other chains such as ethylene glycol chains, as identified above, may be substituted anywhere on the chain. As substituents can themselves be substituted, these groups also include, for example, such compound groups as aryl$C_1$-$C_6$alkyl (e.g., benzyl), halo$C_1$-$C_6$alkyl (e.g., trifluoromethyl), hydroxy$C_1$-$C_6$alkyl (e.g., 2-hydroxy-2-methylbutyl), and $C_1$-$C_6$alkyl-aryl (e.g., tolyl).

Preferred substituents on alkylene groups include halogen or $C_1$-$C_6$ (preferably $C_1$-$C_3$) alkyl groups, which may be optionally substituted with one or two hydroxyl groups, one or two ether groups (O$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present invention, a moiety in a molecule may be optionally substituted with up to five substituents, preferably up to three substituents. Most often, in the present invention moieties which are substituted are substituted with one or two substituents.

As used herein, the terms "aryl" means any carbocyclic aromatic ring system, i.e., any aromatic ring system comprising only carbon atoms as ring atoms. This includes 6-membered monocyclic aryl ring systems and 9-membered or 10-membered fused bicyclic aryl ring systems, and larger fused ring systems, as long as such ring systems comprise at least one 6-membered aromatic carbocyclic ring (i.e., a benzene ring) within the fused ring system, and as long as no ring-atoms are heteroatoms. Thus, the term aryl includes, but is not limited to, phenyl, napthyl, phenanthryl, and anthracenyl.

As used herein, "heteroaryl" means any cyclic heteroaromatic ring system, i.e., any aromatic ring system comprising at least one heteroatom (e.g., N, S, or O) ring atom. This includes 5-membered and 6-membered monocyclic heteroaryl ring systems (e.g., azoles, azines) and 9-membered or 10-membered fused bicyclic heteroaryl ring systems, and larger fused ring systems, as long as such ring systems comprise at least one aromatic carbocyclic or aromatic heterocyclic ring within the fused ring system and at least one heteroatom (e.g., N, S or O) ring-atom within the fused ring system (either in an aromatic ring or non-aromatic ring). Heteroaryl therefore includes, but is not limited to, bicyclic fused ring systems selected from aromatic-heteroaromatic, aromatic-heterocyclic, heteroaromatic-carbocyclic, heterocyclic-aromatic, and heteroaromatic-heteroaromatic, as well as larger fused ring systems comprising some combination of benzene, cycloalkane, heterocycloalkane and heteroaromatic rings. Exemplary heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidinyl, pyrazinyl, pyridazinyl, pyridonyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyridinyl, benzo[b]thiophenyl, 5,6,7,8-tetrahydro-quinolin-3-yl, benzoxazolyl, benzofuranyl, isobenzofuranyl, benzothiazolyl, benzisothiazolyl, benzisoxazolyl, benzimidazolyl, benzothiadiazolyl, thianapthenyl, isothianapthenyl, benzofuranyl, isobenzofuranyl, isoindolyl, indolyl, indolizinyl, indazolyl, isoquinolinyl, quinolinyl, phthalazinyl, quinoxalinyl, quinazolinyl, napthyridinyl, phenanthridinyl, acridinyl, carbazolyl, carbazolinyl, permidinyl, phenanthrolinyl, phenacenyl, pyrrolopyrimidinyl, pyrrolopyridinyl, pyridopyrimidinyl, theinopyrimidinyl, furopyrimidinyl, furopyridyl, furopyrrolyl, pyrazoloxazolyl, thienofuranyl, imidazothiazolyl, imidazopyridyl, imidazotriazyl, imidazopyrimidinyl, pyrazinopyridazinyl, phenothiazinyl, furazanyl, phenoxazinyl, pyrazo benzoxazinyl, azaindolizinyl, dihydroquinolinyl, dihydroisoquinolinyl, tetrahydroquinolinyl, tetrahydroisoquinolinyl, and pyridoxazinyl. It is understood that for heteroaryl systems in which both the ring carbon atoms and ring heteroatoms have open valencies, bonds can be formed to either such atom types (e.g., C-linked or N-linked). For example, where a pyrazolyl ring is one of the group A in the Linker moiety L, the adjacent A groups can be connected to the pyrazolyl ring at either a ring nitrogen atom or at a ring carbon atom.

As used herein, "heterocycloalkyl" means any cyclic nonaromatic ring system comprising at least one heteroatom (e.g., N, S, or O) ring atom. This includes 3- to 12-membered monocyclic and fused bicyclic ring systems, and any larger multi-ring fused ring systems, as long as such ring systems do not comprise any aromatic carbocyclic or aromatic heterocyclic ring. Exemplary heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, piperizin-2-onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8-diazabicyclo[3.2.1]octanyl, 2,5-diazabicyclo[2.2.1]heptanyl, 2,5-diazabicyclo[2.2.2]octanyl, octahydro-2H-pyrido[1,2-a]pyrazinyl, 3-azabicyclo[4.1.0]heptanyl, 3-azabicyclo[3.1.0]hexanyl, 2-azaspiro[4.4]nonanyl, 7-oxa-1-aza-spiro[4.4]nonanyl, 7-azabicyclo[2.2.2]heptanyl, octahydro-1H-indolyl, etc. In general, the heterocycloalkyl group typically is attached to the main structure via a carbon atom or a nitrogen atom. Of course, other heterocycloalkyl groups will be readily apparent to those of skill in the art given the benefit of the present disclosure.

As used herein, "cycloalkyl" means a nonaromatic saturated or unsaturated free radical forming at least one ring consisting essentially of 3 to 10 carbon atoms and a corresponding number of hydrogen atoms. The term "cycloalkyl" therefore includes cycloalkenyl groups, as further defined below. As such, cycloalkyl groups can be monocyclic or polycyclic. Individual rings of such polycyclic cycloalkyl groups can have different connectivities, e.g., fused, bridged, spiro, etc., in addition to covalent bond substitution. Exemplary cycloalkyl groups include cyclopropyl, cyclobutyl, cyclopentyl, cyclohexyl, cycloheptyl, norbornanyl, bicyclo[3.2.1]octanyl, octahydro-pentalenyl, spiro[4.5]decanyl, cyclopropyl, adamantyl, substituted with cyclobutyl, cyclobutyl substituted with cyclopentyl, cyclohexyl substituted with cyclopropyl, etc.

It is understood that when describing the substituents attached in various positions to the core structure described herein, including substituents attached to substituents, in some cases, the substituent may be referred to using the name of the corresponding chemical compound, especially in the case of rings, whereas in some cases the same substituent may be referred to using the name of the corresponding chemical radical (e.g., having an "-yl" suffix), but these terms are interchangeable. For example, when referring to a heteroaryl ring substituent, the terms "pyridine" and "pyridyl" are equivalent, as are the terms "morpholine" and "morpholinyl." The skilled artisan will recognize that such terms are used to denote attachment of, for example, pyridine or morpholine ring at the designated position, thus converting said ring to a pyridyl or morpholinyl substituent (radical) respectively. Absent an indication otherwise, such attachments may be made at any chemically permissible location of the attached ring.

EXAMPLES

Unless otherwise noted, starting materials, reagents, and solvents were obtained from commercial suppliers (e.g., Acros Organics, Sigma-Aldrich, Alfa Aesar, Fluorochem, and Merck) and were used without further purification. Reactions were routinely monitored by thin-layer chromatography (TLC) performed on silica gel 60 $F_{254}$ (layer 0.2 mm) pre-coated aluminum foil (with fluorescent indicator UV254) (Sigma-Aldrich). Developed plates were air-dried and visualized under UV light (254/365 nm) or by using $KMnO_4$ or ninhydrin solutions. Flash column chromatography was performed on Merck silica gel 60 (mesh 230-400). Automated flash chromatographic purifications were performed using Biotage® Selekt (Cartridge: Sfär Silica HC Duo 5 g or 10 g). Preparative TLC purification was performed on Merck silica gel 60 F254 (0.5 mm) pre-coated glass plates (20×20 cm) (Sigma-Aldrich)

$^1$H NMR and $^{13}$C NMR spectra were recorded at room temperature at 400 and 101 MHz, respectively, on a Bruker Avance 400 spectrometer by using TMS or residual solvent peak as internal standard. Chemical shifts are reported in ppm (δ) and the coupling constants (J) are given in Hertz (Hz). Peak multiplicities are abbreviated as follow: s (singlet), bs (broad singlet), d (doublet), dd (double doublet), t (triplet), dt (double triplet), q (quartet), p (pentet), and m (multiplet).

High-Resolution Mass Spectroscopy (HRMS) spectra were registered on Agilent Technologies 6540 UHD Accurate Mass Q-TOF LC-MS system or on Agilent 1290 Infinity Series U-HPLC system (Agilent Technologies, Santa Clara, CA, USA) coupled with a Q-TOF 6540 high-resolution mass spectrometer and 1290 Infinity Series DAD/UV-Vis detector (Agilent Technologies). The purity of all final compounds that were evaluated in biological assays was assessed as >95%, using LC-MS. The analyses were carried out according to the method listed below. The mobile phase was a mixture of water (solvent A) and acetonitrile (solvent B), both containing formic acid at 0.1%. Method: Acquity UPLC BEH C18 1.7 µm (C18, 150×2.1 mm) column at 40° C. using a flow rate of 0.65 mL/min in a 10 min gradient elution. Gradient elution was as follows: 99.5:0.5 (A/B) to 5:95 (A/B) over 8 min, 5:95 (A/B) for 2 min, and then reversion back to 99.5:0.5 (A/B) over 0.1 min. The UV detection is an averaged signal from wavelength of 190 nm to 640 nm and mass spectra are recorded on a mass spectrometer using positive mode electro spray ionization. The chemical names were generated using ChemBioDraw 12.0 from CambridgeSoft.

Compounds described herein may be synthesized as described herein, using modified methods described herein or by methods known to a person of skill in the art.

Chemistry abbreviations: ACN, acetonitrile; Boc, tert-butoxycarbonyl; CD3OD, deuterated methanol; CDCl3, deuterated chloroform; DCE, dichloroethane; DCM, dichloromethane; DEE, diethyl ether; DIPEA, N,N'-diisopropylethylamine; DMA, dimethylacetamide; DMF, dimethylformamide; DMSO, dimethylsulfoxide; DMSO-d6, deuterated dimethylsulfoxide; EA, ethyl acetate; h, hour; EtOH, absolute ethanol; Et3N, triethylamine; HATU, 2-(7-Aza-1H-benzotriazole-1-yl)-1,1,3,3-tetramethyluronium hexafluorophosphate; min, minutes; HRMS, high-resolution mass spectroscopy; MeOH, methanol; NMR, nuclear magnetic resonance; tBu, tert-butyl; tBuOH, tert-butanol; TLC, thin-layer chromatography; PE, petroleum ether; rt, room temperature.

Chemical Synthesis

Compounds of general formula (I) may be prepared by the general synthetic approaches described below (General Scheme 1 and 2), together with synthetic methods known in the art of organic chemistry. In all methods, it is well-understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3' edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I). Specific detailed synthetic procedures for a variety of intermediates and related compounds to those within the scope of the present disclosure can be found in US 2020/0239430, US 2020/0282068, and WO 2020/160295 (and its equivalent U.S. Pat. No. 11,098,025), the contents of each of which are hereby incorporated by reference in their entireties.

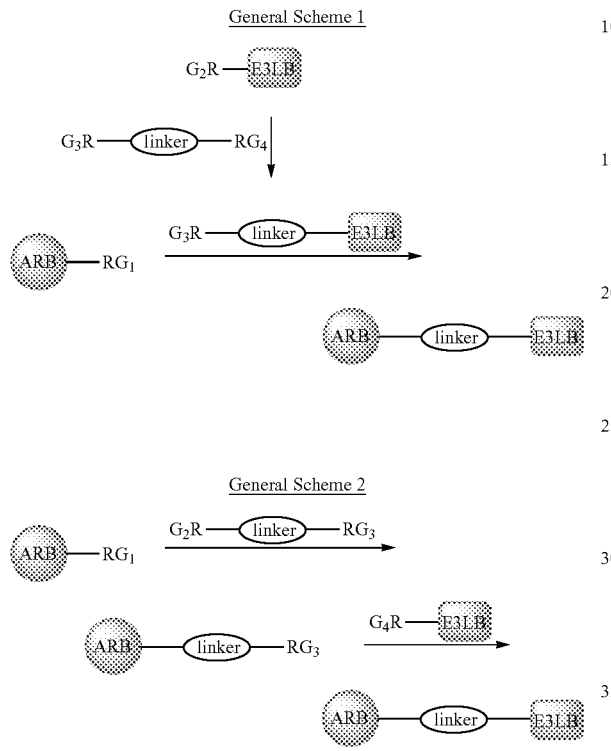

ARB: Androgen Receptor (AR) Binder; E3LB: E3 Ligase Binder.

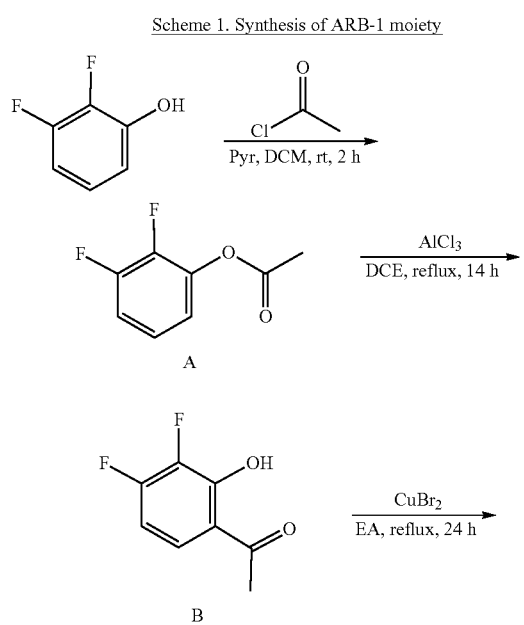

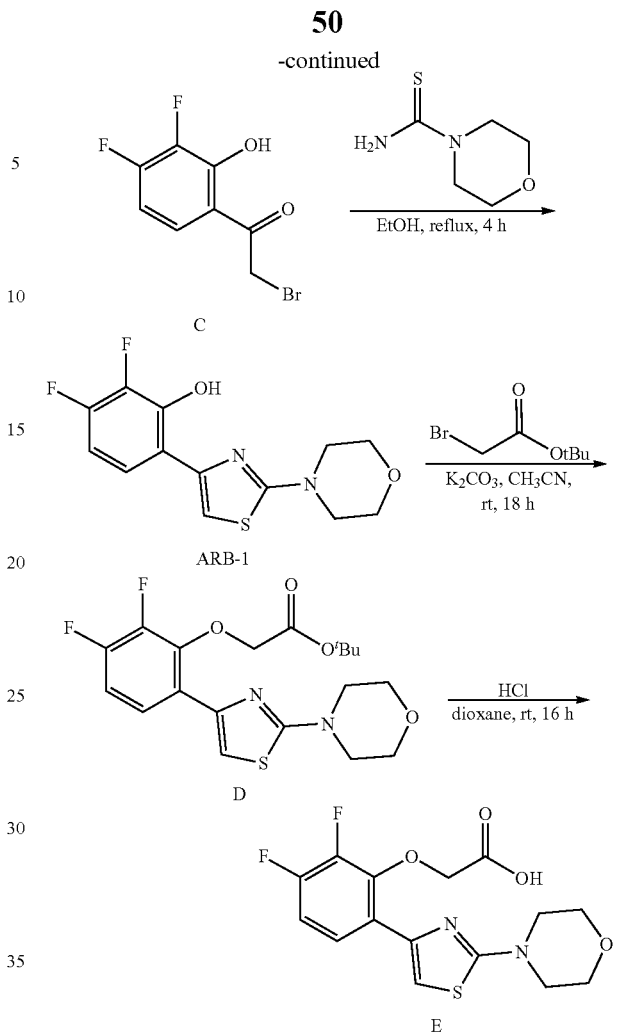

2,3-Difluorophenyl acetate (A)

The titled compound can be prepared according to the process described by Huifang Li et al., *J. Med. Chem.* 2014, 57, 6458-6467.

Acetyl chloride (6.01 mL, 6.63 g, 84.55 mmol) is slowly added at rt to a stirred solution of 2,3-difluorophenol (10.0 g, 76.87 mmol) and pyridine (6.83 mL, 6.68 g, 84.55 mmol) in dry DCM (60.0 mL). After 2 h, the mixture is diluted with 2N HCl (60 mL) and the aqueous layer is separated and extracted with DCM (30 mL×3). The reunited organic phases are washed with brine (20 mL×2), dried over anhydrous $Na_2SO_4$, and concentrated under reduced pressure to afford the titled compound (13.26 g, 99% yield) as a colorless oil. $^1H$ NMR (400 MHz, $CDCl_3$): δ 7.16-7.03 (m, 2H), 6.99-6.83 (m, 1H), 2.37 (s, 3H); $^{13}C$ NMR (101 MHz, $CDCl_3$): δ 167.96, 151.26 (dd, J=10.9, 249.4 Hz), 143.29 (dd, J=14.3, 251.5 Hz), 139.55 (dd, J=2.3, 10.1 Hz), 123.36 (dd, J=5.0, 7.9 Hz), 118.78 (d, J=3.5 Hz), 114.71 (d, J=17.3 Hz), 20.44.

1-(3,4-Difluoro-2-hydroxyphenyl)ethan-1-one (B)

The titled compound can be prepared according to the process described by Gomtsyan, Arthur R. et al., PCT Int. Appl. WO2010045401.

AlCl$_3$ (1.55 g, 11.62 mmol) is added under nitrogen at 0° C. in small portions to a stirred solution of 2,3-difluorophenyl acetate (A) (2.00 g, 11.62 mmol) in DCE (3.0 mL). After addition is completed, the mixture is refluxed for 14 h. After cooling at rt, the solvent is evaporated and the residue diluted with DCM (20 mL). 2N HCl (10 mL) is added, and the mixture is stirred for 20 min. Organic phase is separated, the water extracted with DCM (10 mL×2), and the reunited organic phases are dried over anhydrous Na$_2$SO$_4$ and concentered under reduced pressure to give the titled compound (1.95 g, 97% yield) as a brownish solid. $^1$H NMR (400 MHz, CDCl$_3$): δ 12.59 (d, J=1.4 Hz, 1H), 7.55 (ddd, J=2.3, 5.5, 9.1 Hz, 1H), 6.86-6.63 (m, 1H), 2.65 (s, 3H); $^{13}$C NMR (101 MHz, CDCl$_3$): δ 203.66, 157.02, 154.88 (dd, J=9.7, 257.9 Hz), 139.98 (dd, J=13.7, 249.7 Hz), 125.92 (dd, J=4.5, 10.0 Hz), 117.77, 107.24 (d, J=18.7 Hz), 26.78.

2-Bromo-1-(3,4-difluoro-2-hydroxyphenyl)ethan-1-one (C)

The titled compound can be prepared according to the process described by Huifang Li et al., *J. Med. Chem.* 2014, 57, 6458-6467.

A solution of 1-(3,4-difluoro-2-hydroxyphenyl)ethan-1-one (B) (1.95 g, 11.33 mmol) in EA (40.0 mL) is added dropwise at rt to a stirred suspension of CuBr$_2$ (3.03 g, 13.59 mmol) in EA (40 mL). After 24 h of reflux, the mixture is allowed to cool to rt, filtered over Celite, and the filtrate is evaporated to dryness. The crude residue is purified by flash column chromatography on SiO$_2$ (PE/EA, 95:5) to give the titled compound (1.55 g, 69% yield) as yellow solid. $^1$H NMR (400 MHz, CDCl$_3$): δ 12.10-11.84 (m, 1H), 7.58 (ddd, J=2.2, 5.4, 8.9 Hz, 1H), 6.93-6.65 (m, 1H), 2.65 (s, 2H); $^{13}$C NMR (101 MHz, CDCl$_3$): δ 196.41, 155.36 (dd, J=9.7, 259.7 Hz), 154.11 (dd, J=5.6, 9.6 Hz), 140.29 (dd, J=13.9, 251.0 Hz), 125.92 (dd, J=4.6, 10.1 Hz), 115.13, 107.90 (d, J=19.1 Hz), 29.31.

2,3-Difluoro-6-(2-morpholinothiazol-4-yl)phenol (ARB-1)

The titled compound can be prepared according to the process described by Huifang Li et al., *J. Med. Chem.* 2014, 57, 6458-6467.

Morpholine-4-carbothioamide (0.330 g, 2.26 mmol) is added in small portions to a stirred solution of compound 2-bromo-1-(3,4-difluoro-2-hydroxyphenyl)ethan-1-one (C) (0.568 g, 2.26 mmol) in absolute EtOH (10 mL) at 0° C. When addition is completed, the mixture is refluxed for 4 h. After cooling to rt, the mixture is evaporated to dryness and NaHCO$_3$ saturated solution (20 mL) is added to pH 8. The aqueous phase is extracted with EA (10 mL×3), the reunited organic phases are dried over anhydrous Na$_2$SO$_4$ and concentrated under reduced pressure to give a solid which was triturated with DEE and filtered affording the titled compound (0.590 g, 87% yield) as a light-yellow solid. $^1$H NMR (400 MHz, CDCl$_3$): δ 12.43 (s, 1H), 7.24 (ddd, J=2.3, 5.6, 8.5 Hz, 1H), 6.76 (s, 1H), 6.66 (td, J=7.2, 9.3 Hz, 1H), 4.00-3.84 (m, 4H), 3.63-3.43 (m, 4H); $^{13}$C NMR (101 MHz, CDCl$_3$): δ 171.13, 151.23 (dd, J=10.4, 247.9 Hz), 148.09, 147.25-146.05 (m), 140.72 (dd, J=14.2, 244.7 Hz), 119.63 (dd, J=4.5, 8.7 Hz), 115.71, 106.97 (d, J=18.4 Hz), 100.25 (d, J=1.7 Hz), 65.90 (2C), 48.31 (2C).

Tert-butyl 2-(2,3-difluoro-6-(2-morpholinothiazol-4-yl)phenoxy)acetate (D)

The titled compound can be prepared according to the process described in US 2020/0282068.

Tert-butyl bromoacetate (0.434 mL, 0.575 g, 2.95 mmol) is added to a stirred suspension of 2,3-difluoro-6-(2-morpholinothiazol-4-yl)phenol (ARB-1) (0.800 g, 2.68 mmol) and K$_2$CO$_3$ (0.927 g, 6.71 mmol) in ACN (10.0 mL). The suspension is stirred for 18 h at rt, filtered, and the filtrate is evaporated to dryness. Residue is purified by flash column chromatography on SiO$_2$ (PE/EA, 95:5 to 90:10) to afford the titled compound (0.800 g, 73% yield) as a yellow solid. $^1$H NMR (400 MHz, CDCl$_3$): δ 7.92 (ddd, J=2.3, 6.2, 8.8 Hz, 1H), 7.68 (s, 1H), 7.10-6.87 (m, 1H), 4.67 (d, J=1.7 Hz, 2H), 4.00-3.79 (m, 4H), 3.68-3.47 (m, 4H), 1.53 (s, 9H); $^{13}$C NMR (101 MHz, CDCl$_3$): δ 169.77, 167.40, 150.32 (dd, J=11.8, 249.8 Hz), 145.30, 144.64-144.23 (m), 143.98 (dd, J=14.4, 246.1 Hz), 124.35, 124.04 (dd, J=3.9, 7.8 Hz), 111.42 (d, J=17.0 Hz), 107.71, 82.55, 70.00 (d, J=7.5 Hz), 66.22 (2C), 48.61 (2C), 28.09 (3C).

2-(2,3-Difluoro-6-(2-morpholinothiazol-4-yl)phenoxy)acetic acid (E)

The titled compound can be prepared according to the process described in US 2020/0282068.

A solution of 4N HCl in dioxane (15 mL) is added to tert-butyl 2-(2,3-difluoro-6-(2-morpholinothiazol-4-yl)phenoxy)acetate (D) (0.780 g, 1.89 mmol) and the resulting suspension is stirred at rt for 16 h. The solvent ias evaporated to dryness and the residue was triturated with DEE. The solids are collected by filtration and dried under vacuo to afford the titled compound (0.672 g, 91% yield) as light-yellow solid. $^1$H NMR (400 MHz, CD$_3$OD): δ 7.48 (ddd, J=2.3, 5.7, 8.1 Hz, 1H), 7.27 (s, 1H), 7.18 (td, J=7.5, 9.2 Hz, 1H), 5.01 (d, J=1.5 Hz, 2H), 4.02-3.86 (m, 4H), 3.86-3.67 (m, 4H); $^{13}$C NMR (101 MHz, CD$_3$OD): δ 171.72, 169.44, 152.57 (dd, J=11.6, 252.2 Hz), 144.55 (d, J=1.7 Hz), 143.30 (dd, J=15.0, 248.0 Hz), 136.41 (d, J=13.3 Hz), 124.82 (dd, J=3.9, 8.6 Hz), 118.47, 111.66 (d, J=18.2 Hz), 106.15, 69.24 (d, J=9.0 Hz), 65.05 (2C), 49.17 (2C).

Scheme 2. Synthesis of E3LB-1 moiety

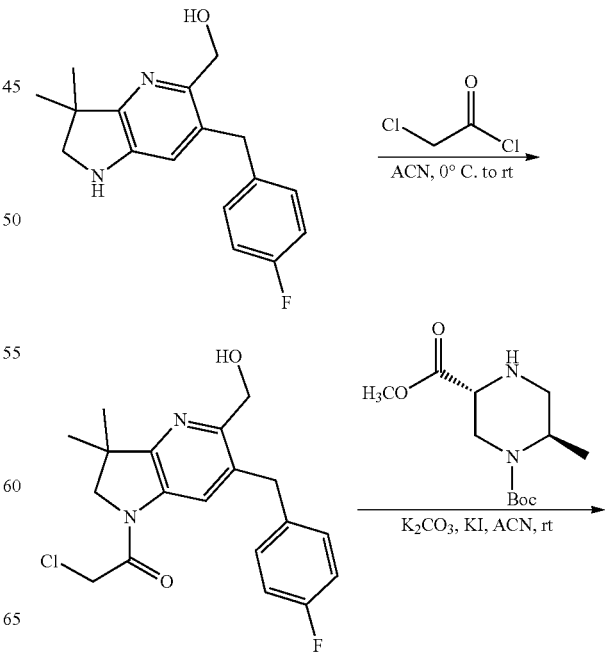

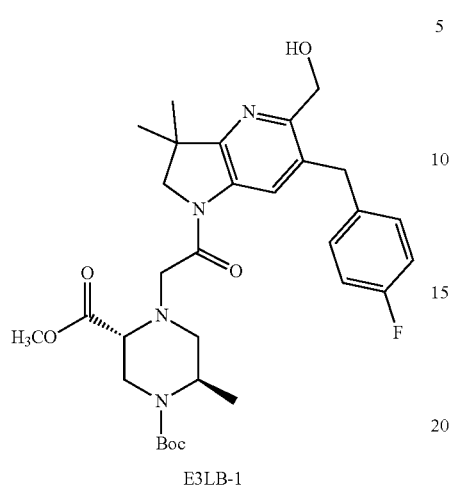
E3LB-1
Scheme 3. Synthesis of Examples 1-4.
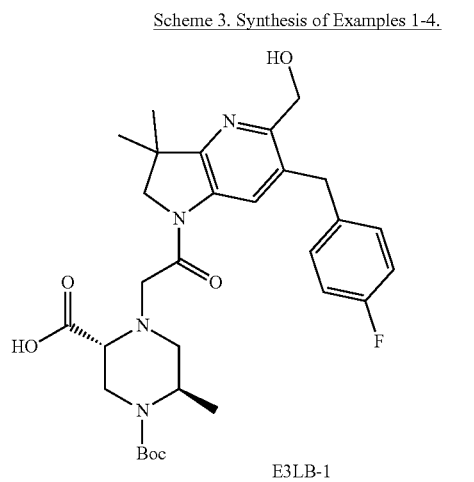
E3LB-1
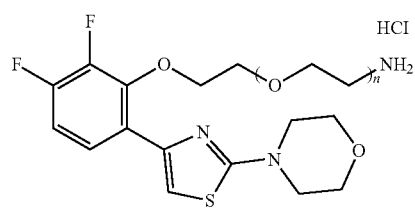
n = 1, 2, 3, 4
HATU, DIPEA, DMF, rt
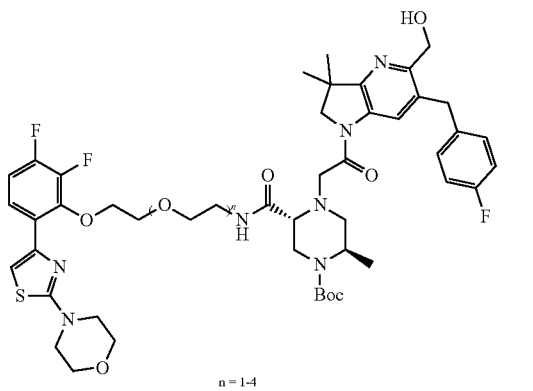
n = 1-4
HCl, dioxane, rt
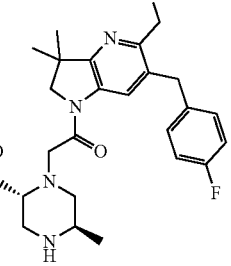
Example 1 n = 1
Example 2 n = 2
Example 3 n = 3
Example 4 n = 4
ARB-1
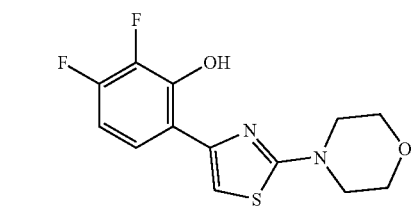
PPh₃, DIAD, dry THF, 0 °C-16h
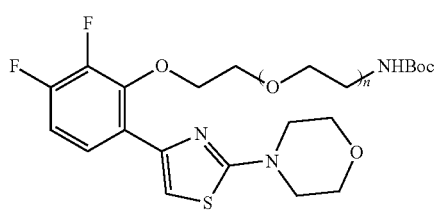
n = 1
n = 2
n = 3
n = 4
HCl
dioxane, rt,
overnight -continued

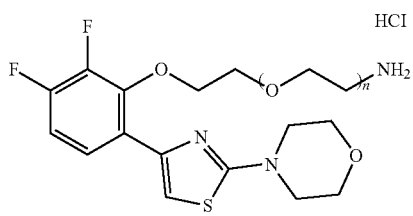

n = 1
n = 2
n = 3
n = 4

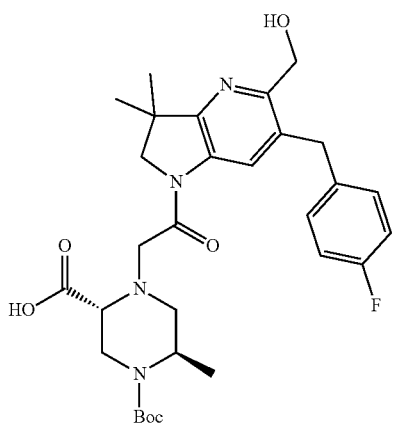

E3LB-1

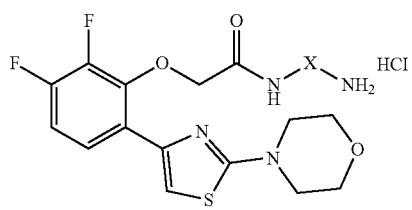

n = 1, 2, 3, 4

———————————→
HATU, DIPEA, DMF, rt

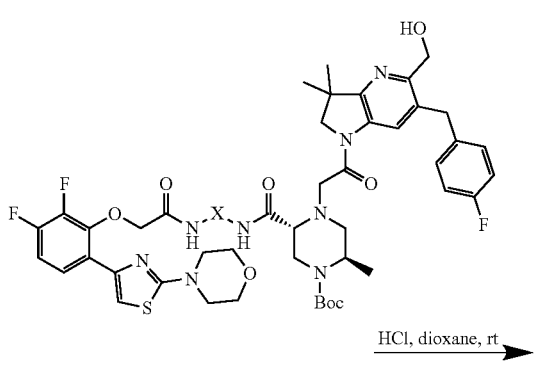

HCl, dioxane, rt
———————————→

-continued

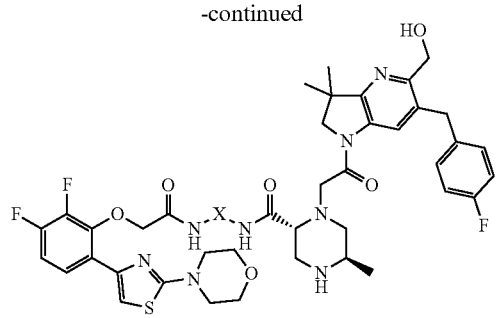

Example 5 X = (CH$_2$)$_3$
Example 6 X = (CH$_2$)$_4$
Example 7 X = (CH$_2$)$_5$
Example 8 X = (CH$_2$)$_6$
Example 9 X = (CH$_2$)$_8$
Example 10 X = (CH$_2$)$_{10}$ Experimental Example 1: 22Rv1 Cell Proliferation Assays The human prostate cancer cell line, 22Rv1 has been reported to express a high level of AR-V7. According to one procedure, 22Rv1 is seeded at 50,000 cells/well on a 24-well plate in quadruplicate and treated with test compounds in concentrations ranging up to 20 μM for four days. Standard culture media is RPMI-1640 supplemented with 10% fetal bovine serum. The test compound initially is dissolved in DMSO at 50 mM. This stock solution is then diluted as needed for the indicated concentrations. At the end of the four-day period, cells are harvested using 1% trypsin and counted using an automated cell counter.

Experimental Example 2: Immunoblot

Immunoblot may be carried out to determine the effect of the test compound on AR-V7. 22Rv1 is plated at 200,000 cell/well on a 6-well plate and cultured as described with 10 μM test compound. After four days of treatment, cells are harvested using a cell scraper and lysed in a standard fashion using SDS. After removing debris via centrifuge, 30 μg of protein is loaded onto SDS-PAGE gel. After electrophoresis, protein is transferred to a nylon membrane and ECL is carried out using primary antibody against AR-V7 (ThermoFisher Scientific, cat #NC0752138). Protein bands are visualized using the commercially available Enhanced Chemiluminescence (ECL) kit (ThermoFisher).

Experimental Example 3

Compounds according to the present disclosure ("Test Compound") may be tested for in vitro and/or in vivo efficacy according to one or more of the procedures outlined below.

Cell Culture. Human CaP cell lines, LNCaP, 22Rv1, VCaP, PC3, and DU145 are obtained from the American Type Culture Collection (ATCC) and maintained in the standard culture media: RPMI-1640 supplemented with 10% fetal bovine serum (FBS). LNCaP, 22Rv1, and VCaP are androgen-responsive cell lines, while PC3 and DU145 are not. To establish SAT resistant CaP cell lines, LNCaP, 22Rv1, and VCaP are treated continuously with 10-50 μM abiraterone, apalutamide, darolutamide, or enzalutamide. After 3-6 months, stable cell lines are established and designated as LNCaP-Abi$^R$, LNCaP-Apa$^R$, LNCaP-Daro$^R$, LNCaP-Enz$^R$, VCaP-Abi$^R$, VCaP-Apa$^R$, VCaP-Daro$^R$, VCaP-Enz$^R$, 22Rv1-Abi$^R$, 22Rv1-Apa$^R$, 22Rv1-Daro$^R$, and 22Rv1-Enz$^R$. Unless otherwise specified, the standard culture media for these SAT-resistant cell lines included 10 µM of their respective SAT. For the proteasome inhibitor study, the inhibitors MG132 and Epoxomicin are used. The E3 ligase inhibitors Heclin, Nutlin 3a, Thalidomide, and VH298 are used. Cell lines obtained from ATCC are confirmed by checking their morphology using optical microscopy, establishing baselines for cell proliferation, verifying species of origin using isoenzymology, and characterizing the cell's DNA fingerprint using short tandem repeat (STR) profiling. Mycoplasma contamination is also assessed using a PCR based detection system.

Apoptosis Assay. An apoptosis assay is carried out using the ThermoFisher ApoDETECT Annexin V-FITC kit following the protocol recommended by the vendor. Briefly, after treatment with 1 µM of Test Compound for 3 to 24 hours, cells are fixed with 80% ethanol and washed with PBS three times. Then, fixed cells are incubated with Annexin V-FITC in PBS solution for 30 minutes at room temperature. After washing three times with PBS, cells are treated with 300 nM DAPI in PBS for 5 minutes at room temperature. Finally, after washing three times with PBS, mounting solution is added and the cells are visualized using immunofluorescence microscopy. Next, a TUNEL assay is performed using Promega DeadEnd Fluorometric TUNEL system. After treatment with Test Compound and fixation as described above in the Annexin-V experiment, 100 µl of equilibration buffer is incubated for 10 min. Then, 50 µl of TdT reaction mix is added and incubated for 60 min at 37° C. in a humidified chamber. Finally, stop solution is added and samples are mounted on slides using mounting medium. To assess non-specific cytotoxicity, an LDH assay kit is used.

Transient Transfections. One µg of a plasmid containing cDNA of AR-V7 or AR-FL is transfected into indicated the CaP cell lines on 6-well plates. Three µl of lipofectamine 3000 is used for each transfection.

Immunoblot Analysis. CaP cells are collected and lysed with the lysis buffer (20 mM Tris-HCl (pH 7.5), 150 mM NaCl, 1 mM Na$_2$EDTA, 1 mM EGTA, 1% Triton, 2.5 mM sodium pyrophosphate, 1 mM beta-glycerophosphate, 1 mM Na$_3$VO$_4$, and 1 µg/ml leupeptin) containing 1 mM phenylmethylsulfonyl fluoride (PMSF). Cell lysates are then centrifuged and protein in the supernatant is quantified. After separating 25-50 m of protein using SDS-PAGE, samples are incubated with AR-V7, GR, PR, ERa, AR-FL, ubiquitin, or (3-actin antibodies. For AR-V7, AR-FL, PR, GR, and ERa immunoblots, primary antibody is diluted 1:1000 in 5% skim milk. For the (3-actin immunoblot, 1:10000 diluted primary antibody is used. All membranes are incubated overnight at 4° C. Following the incubation with appropriate secondary antibody, immunoblots are analyzed using SuperSignal West Femto Maximum Sensitivity Substrate (ThermoFisher).

In Vivo Study. To explore the therapeutic potential of test compounds, 22Rv1, 22Rv1-Enz$^R$, VCaP, and VCaP-Enz$^R$ are injected into nu/nu immunodeficient mice. When the resulting tumors reached an average size of 3 mm in diameter, all animals are surgically castrated via bilateral orchiectomy and divided into four groups of five mice each. For anesthesia, 3% isoflurane gas inhalation is used. Tumor size was measured using calipers and tumor volume was calculated using the formula: tumor volume=length×width$^2$/0.361.

Mice are then treated daily with test compound with or without enzalutamide via the indicated route (intratumoral, intraperitoneal, or oral) for five to six weeks. At the end of the study, all animals are sacrificed and tumors are harvested and analyzed. Statistical significance is calculated using the Student's t-test for paired comparisons of experimental groups and, where appropriate, by Wilcoxon rank sum test, and by 2-way ANOVA. In vitro experiments are repeated a minimum of three times.

Experimental Example 4: 22Rv1-Enz$^R$ Cell Proliferation Assays

Selected compounds may be tested in the human prostate cancer cell line, 22Rv1-Enz$^R$, as described in Geun Taek Lee et al., *Molecular Cancer Therapeutics*, 20:490-9 (2021). These procedures are similar to that described in Experimental Example 1, above, except that the assay conditions are a 6-day culture with cell media changed every 24 hours.

The results demonstrate that the test compounds inhibited proliferation in a concentration dependent manner. In the following Table (half maximal growth inhibition constant, GIC$_{50}$): (+)–GIC$_{50}$<200 µM; (++)–GIC$_{50}$<100 µM; (+++)–GIC$_{50}$<10 µM.

TABLE 2

| Compound of Example | 22Rv1-Enz$^R$ proliferation assay GIC$_{50}$ µM |
|---|---|
| 1 | TBD |
| 2 | TBD |
| 3 | TBD |
| 4 | TBD |
| 5 | TBD |
| 6 | TBD |
| 7 | TBD |
| 8 | TBD |
| 9 | TBD |
| 10 | TBD |

What is claimed is:

1. A compound having a chemical structure ARB-L-E3LB, wherein ARB is an AR binding moiety that does not bind to a ligand binding domain, E3LB is an E3 ligase binding moiety, and L is a linker coupling the AR binding moiety to the E3 ligase binding moiety, and wherein:
the E3LB moiety is a pyrrolo[3,2-b]pyridine cIAP-class ubiquitin ligase binding moiety having the following structure:

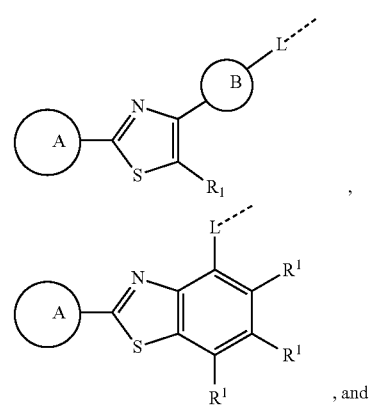

, and

-continued

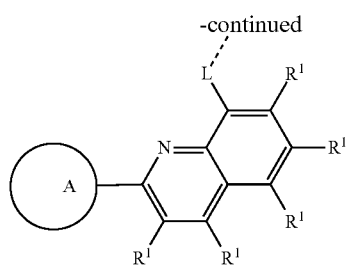

and
wherein the AR binding moiety is selected from:

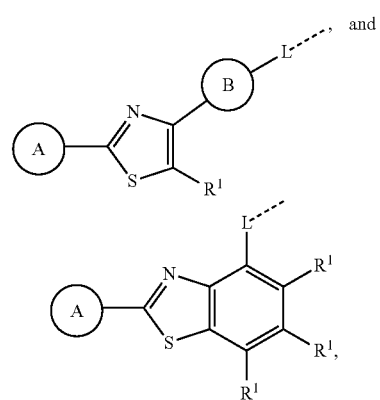

wherein:
A is 3-10 membered heterocycloalkyl ring with 1-4 heteroatoms, optionally substituted by one or more groups selected from halo, hydroxy, nitro, cyano, $C_{1-6}$ alkyl, halo$C_{1-6}$ alkyl, $C_{1-6}$ alkoxy, and $C_{3-6}$ cycloalkyl;
B is phenyl or imidazolyl, each optionally substituted by one or more groups selected from halo, hydroxy, nitro, cyano, $C_{1-6}$ alkyl, halo$C_{1-6}$ alkyl, $C_{1-6}$ alkoxy, and $C_{3-6}$ cycloalkyl; and
each $R^1$ is independently selected from H, halo, and hydroxy.

2. The compound of claim 1, wherein the AR binding moiety is:

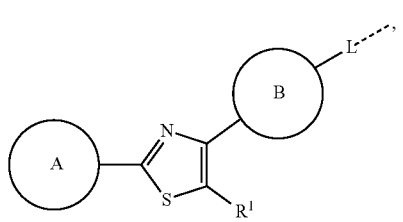

wherein:
A is morpholinyl, piperazinyl, N-methylpiperazinyl, piperidinyl, or pyrrolidinyl, optionally substituted by one or more groups selected from halo, hydroxy, nitro, cyano, $C_{1-6}$ alkyl, halo$C_{1-6}$ alkyl, $C_{1-6}$ alkoxy, and $C_{3-6}$ cycloalkyl;
B is phenyl, optionally substituted by one or more groups selected from halo, hydroxy, nitro, cyano, $C_{1-6}$ alkyl, halo$C_{1-6}$ alkyl, $C_{1-6}$ alkoxy, and $C_{3-6}$ cycloalkyl; and
$R^1$ is H, halo, hydroxy, or $C_{1-6}$ alkyl.

3. The compound according to claim 2, wherein A is:

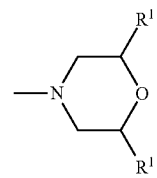

wherein $R^1$ is H, halo, or $C_{1-6}$ alkyl; and
wherein B is:

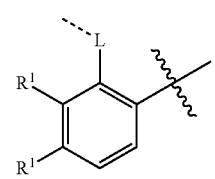

wherein $R^1$ is H, halo, or $C_{1-6}$ alkyl.

4. The compound according to claim 1, wherein the AR binding moiety is selected from:

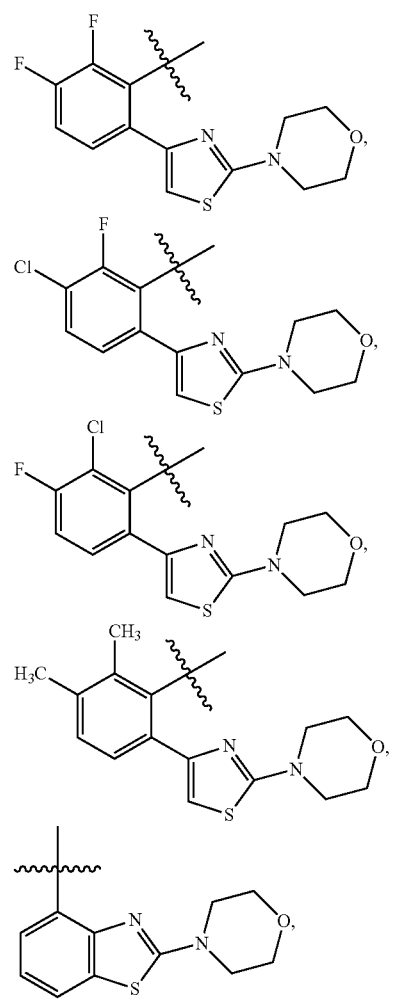

-continued

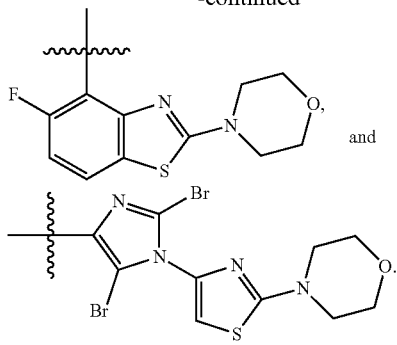

and

5. The compound according to claim 1, wherein the linker ("L") consists of a chemical structural unit represented by the formula $-A_q-$, in which q is an integer greater than 1, and each A is independently selected from the group consisting of: a bond, $CR^{L1}R^{L2}$, O, S, SO, $SO_2$, $NR^{L3}$, $SO_2NR^{L3}$, $SO_2R^{L3}$, $CONR^{L3}$, $NR^{L3}CONR^{L4}$, $NR^{L3}SO_2NR^{L4}$, CO, $SiR^{L1}R^{L2}$, $P(O)R^{L1}$, $P(O)OR^{L1}$, $NR^{L3}(=NCN)NR^{L4}$, $NR^{L3}C(=NCN)$, and $NR^{L3}C(C=NO_2)NR^{L4}$; and wherein: $R^{L1}$, $R^{L2}$, $R^{L3}$, $R^{L4}$ and $R^{L5}$ are each independently selected from the group consisting of H, halo, $C_{1-8}$ alkyl, $OC_{1-8}$ alkyl, $SC_{1-8}$ alkyl, $NHC_{1-8}$ alkyl, $N(C_{1-8}$ alkyl$)_2$, $C_{3-11}$ cycloalkyl, aryl, heteroaryl, 3-6 membered heterocycloalkyl, $OC_{1-8}$ cycloalkyl, $SC_{1-8}$ cycloalkyl, $NHC_{1-8}$cycloalkyl, $N(C_{1-8}$ cycloalkyl$)_2$, $N(C_{1-8}$ cycloalkyl)($C_{1-8}$ alkyl), OH, $NH_2$, SH, $SO_2C_{1-8}$ alkyl, $P(O)(OC_{1-8}$ alkyl)($C_{1-8}$ alkyl), $P(O)(OC_{1-8}$ alkyl$)_2$, $CC-C_{1-8}$ alkyl, CCH, $CH=CH(C_{1-8}$ alkyl), $C(C_{1-8}$ alkyl$)=CH(C_{1-8}$ alkyl), $C(C_{1-8}$ alkyl$)=C(C_{1-8}$ alkyl$)_2$, $Si(OH)_3$, $SiC(_{1-8}$ alkyl$)_3$, $Si(OH)(C_{1-8}$ alkyl$)_2$, $COC_{1-8}$ alkyl, $CO_2H$, CN, halo$C_{1-8}$ alkyl (e.g., $CF_3$, $CHF_2$, $CH_2F$), $NO_2$, $SF_5$, $SO_2NHC_{1-8}$ alkyl, $SO_2NHC_{1-8}$alkyl, $SO_2N(C_{1-8}$alkyl$)_2$, $SONHC_{1-8}$ alkyl, $SON(C_{1-8}$ alkyl$)_2$, $CONHC_{1-8}$ alkyl, $CON(C_{1-8}$ alkyl$)_2$, $N(C_{1-8}$ alkyl)$CONH(C_{1-8}$alkyl), $N(C_{1-8}$ alkyl)$CON(C_{1-8}$ alkyl$)_2$, $NHCONH(C_{1-8}$ alkyl), $NHCON(C_{1-8}$ alkyl$)_2$, $NHCONH_2$, $N(C_{1-8}$ alkyl)$SO_2NH(C_{1-8}$ alkyl), $N(C_{1-8}$ alkyl)$SO_2N(C_{1-8}$ alkyl$)_2$, $NHSO_2NH(C_{1-8}$ alkyl), $NHSO_2N(C_{1-8}$ alkyl$)_2$ and $NHSO_2NH_2$; and wherein $R^{L1}$ and $R^{L2}$ each, independently may be linked to another A group to form a cycloalkyl and or heterocycloalkyl moiety that can be further substituted with 0-4 $R^{L5}$ groups.

6. The compound of claim 5, wherein q is an integer from 1 to 30.

7. The compound of claim 5, wherein the linker L is a flexible linker.

8. The compound of claim 5, wherein the units A are selected from $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, and CO.

9. The compound of claim 8, wherein the units A are selected from $CR^{L1}R^{L2}$, O, $NR^{L3}$, $CONR^{L3}$, and CO.

10. The compound of claim 9, wherein the linker L is selected from:

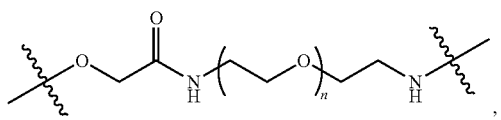

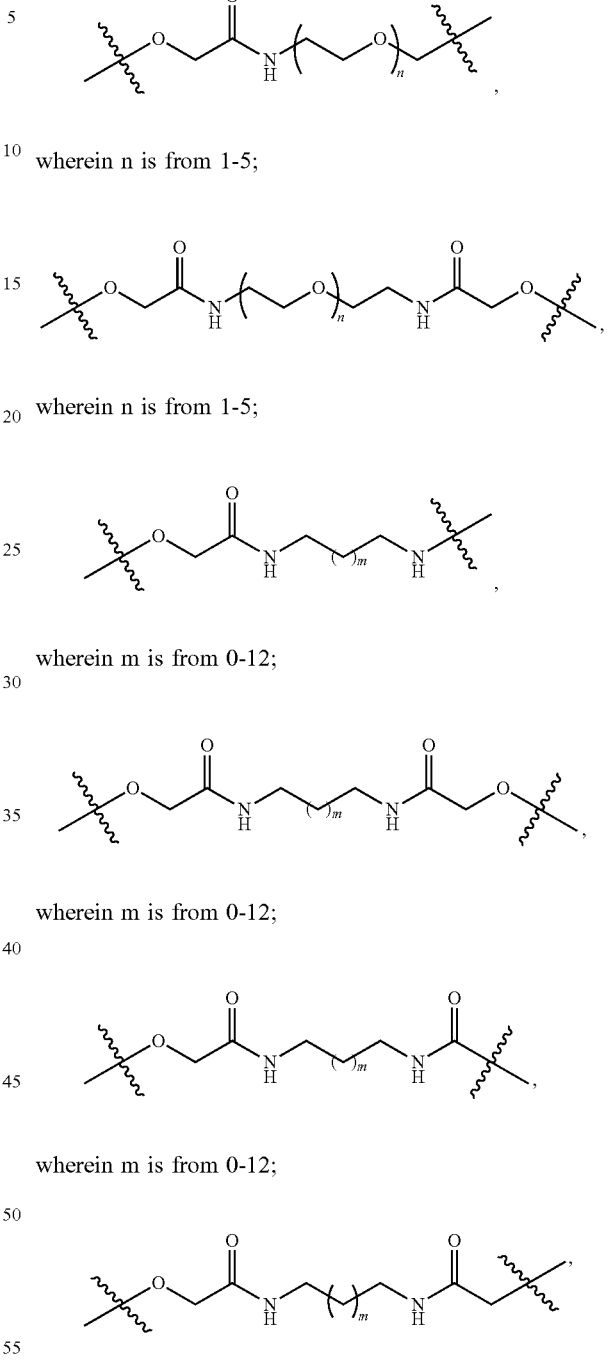

wherein n is from 1-5;

wherein n is from 1-5;

wherein n is from 1-5;

wherein m is from 0-12;

wherein m is from 0-12;

wherein m is from 0-12;

wherein m is from 2-4;

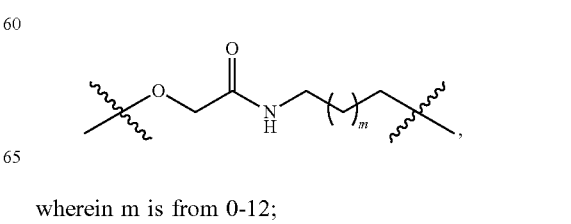

wherein m is from 0-12;

wherein m is from 0-10;

wherein n is from 1-5;

wherein n is from 1-5;

wherein n is from 1-5;

wherein m is from 0-10;

wherein m is from 0-10;

wherein m is from 0-10;

wherein n is from 1-5;

wherein n is from 1-5;

wherein n is from 1-5;

wherein n is from 1-5;

wherein n is from 1-5;

wherein m is from 1-12;

wherein m is from 1-12;

wherein m is from 1-12; and wherein m is from 0-10.

11. The compound according to claim 1, wherein the compound comprises:

the AR binding moiety

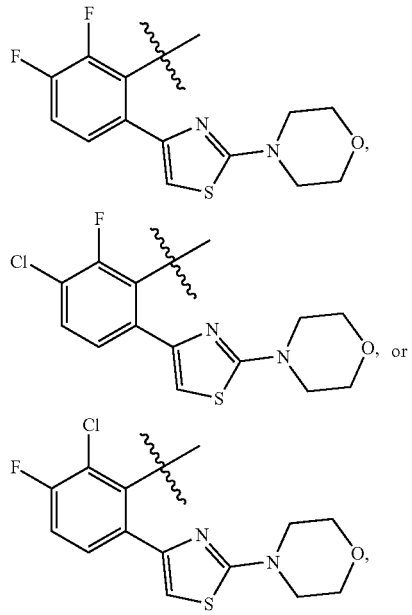

the E3 ligase binding moiety

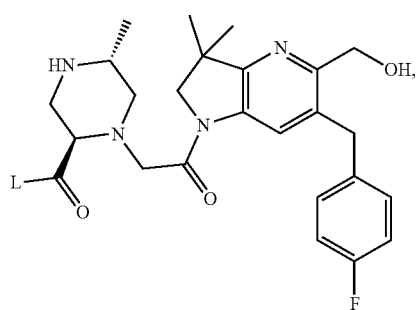

and a linker selected from:

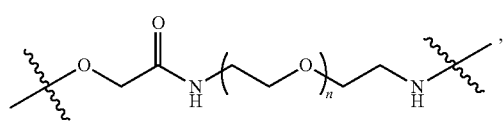

wherein n is from 1-5;

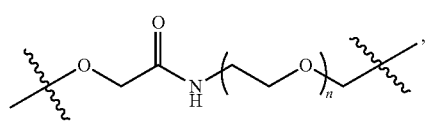

wherein n is from 1-5;

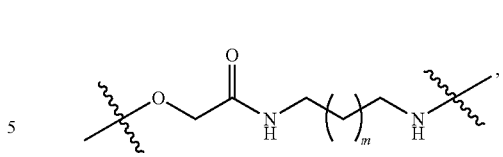

wherein m is from 0-12;

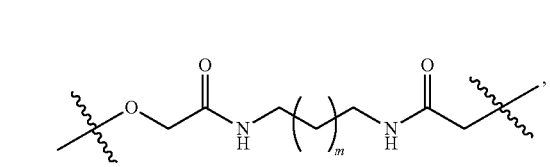

wherein m is from 2-4;

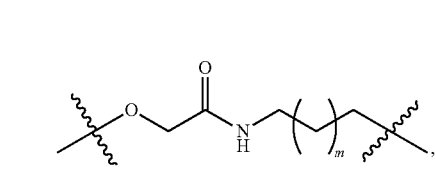

wherein m is from 0-12;

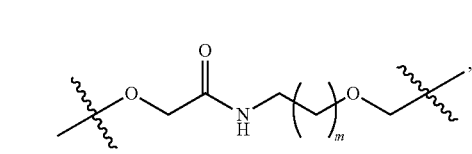

wherein m is from 0-10;

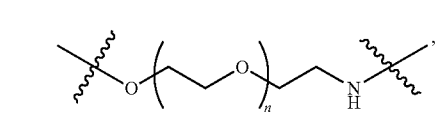

wherein n is from 1-5; and

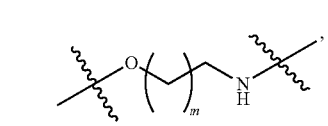

wherein m is from 1-12.

12. The compound according to claim 11, wherein the linker L is selected from:

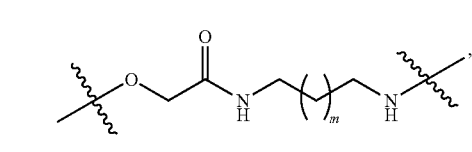

wherein m is from 0-8; and

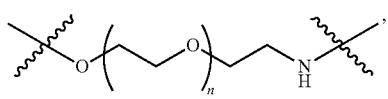
wherein n is from 1-3.
13. A compound selected from the group consisting of:
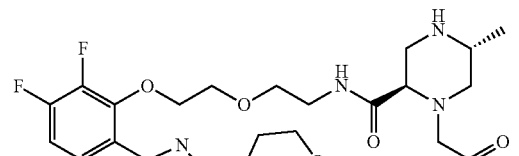
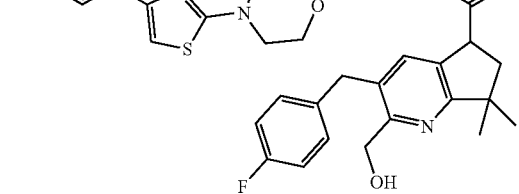
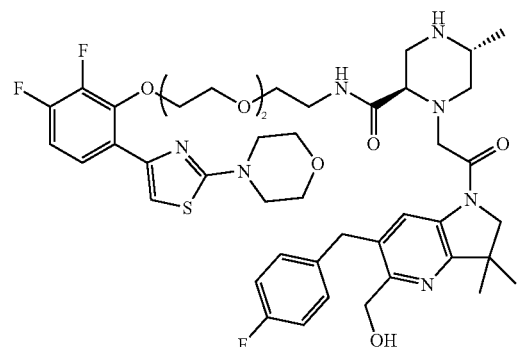
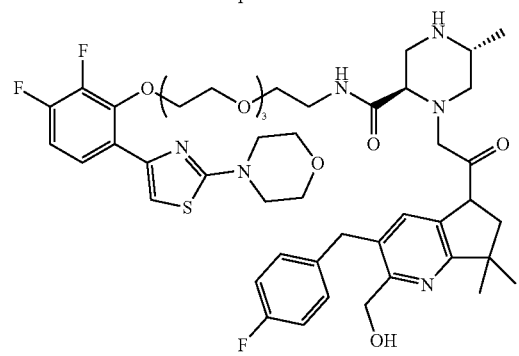
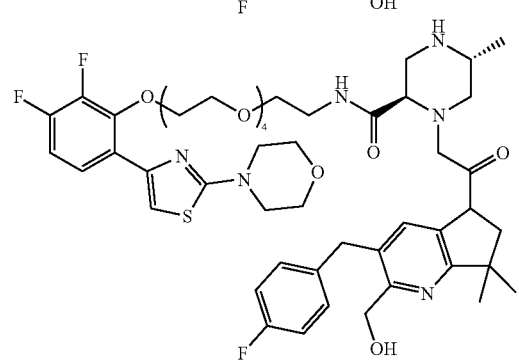
-continued
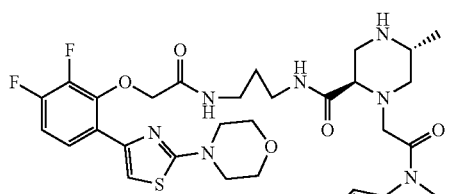
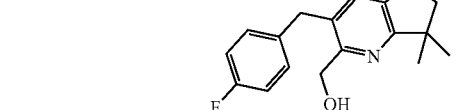
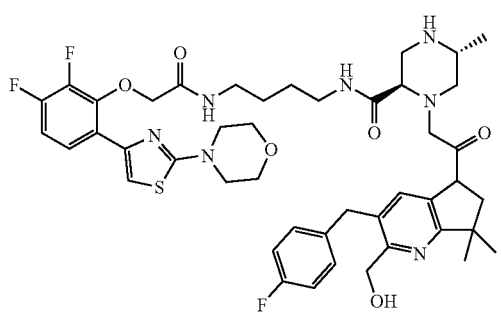
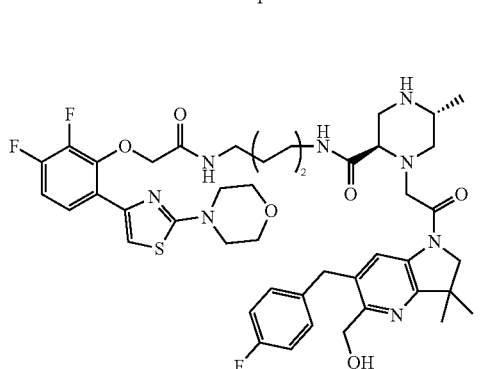
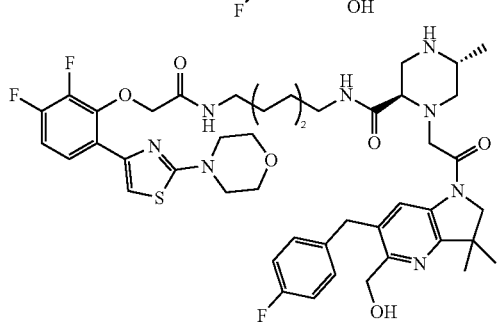
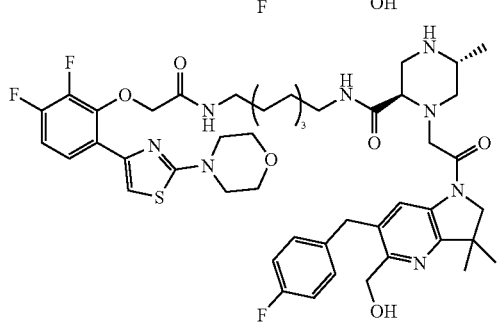

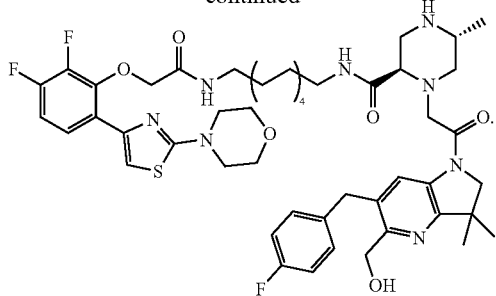

14. A pharmaceutical composition comprising a compound according to claim 1, and a pharmaceutically acceptable carrier, additive and/or excipient.

15. A method of treating a disease state or condition in a patient wherein dysregulated protein activity is responsible for said disease or condition, wherein the disease or condition is a cancer identified as having a mutation resulting, or expected to result in, overexpression of the androgen receptor, said method comprising administering an effective amount of a compound according to claim 1, to a patient in need thereof.

16. A method of degrading an androgen receptor in a cell, said method comprising administering an effective amount of a compound according to claim 1, to such cell.

17. A method of inducing apoptosis in a cell, said method comprising administering an effective amount of a compound according to claim 1, to such cell.

18. The method according to claim 16, wherein the cell is a cancer cell, and wherein the androgen receptor is a mutated androgen receptor selected from AR-V1 to AR-V15 splice variants.

19. The method according to claim 17, wherein the cell is a cancer cell.

* * * * *

UNITED STATES PATENT AND TRADEMARK OFFICE
CERTIFICATE OF CORRECTION

PATENT NO. : 11,981,672 B2
APPLICATION NO. : 17/931843
DATED : May 14, 2024
INVENTOR(S) : Desantis et al.

It is certified that error appears in the above-identified patent and that said Letters Patent is hereby corrected as shown below:

In the Specification

Column 5, Lines 28-38,

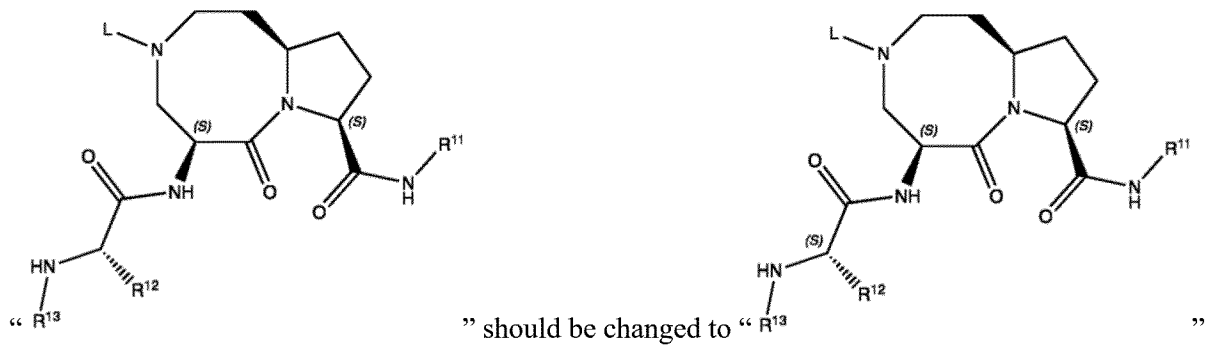

Column 10, Line 16, "S, SO," should be changed to "O, S, SO,"

Column 10, Line 18, "P(O)OR$^{L1}$," should be changed to "P(O)R$^{L1}$, P(O)OR$^{L1}$,"

Column 22, Line 36, "R$^{L3}$, and R$^{L5}$," should be changed to "R$^{L3}$, R$^{L4}$, and R$^{L5}$,"

Column 23, Lines 2-3, "eroaryl. 1.28 Any of compounds 1.15-1.27," should be changed to "eroaryl.
1.28 Any of compounds 1.15-1.27,"

Column 34, Lines 12-15, 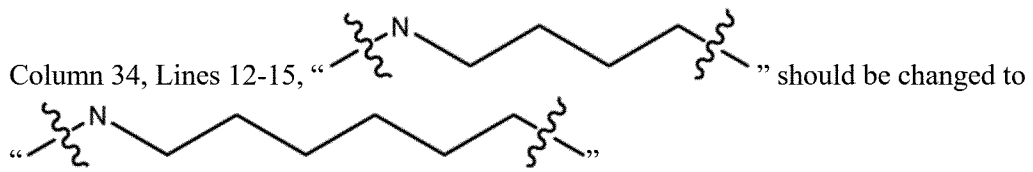

Signed and Sealed this
Twenty-seventh Day of August, 2024

Katherine Kelly Vidal
*Director of the United States Patent and Trademark Office*

Column 34, Lines 16-19, "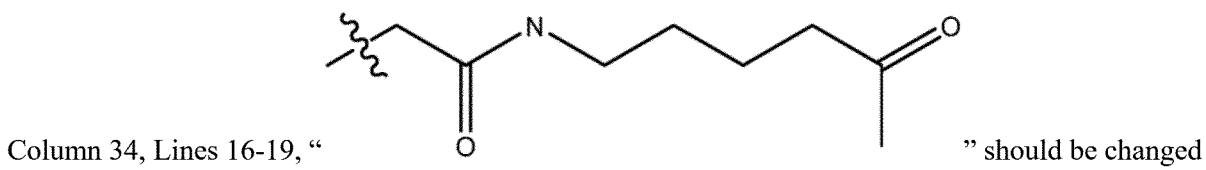" should be changed to "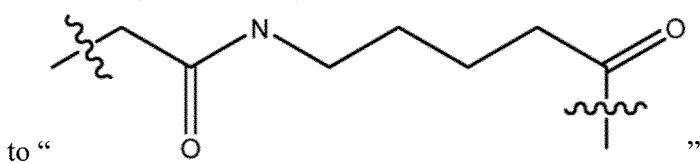"

Column 34, Lines 37-42, "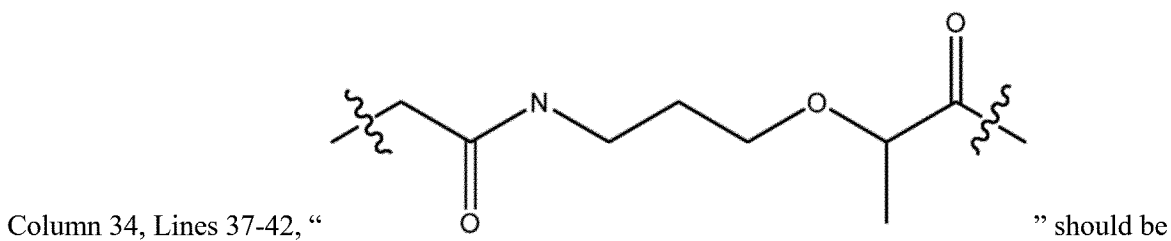" should be changed to "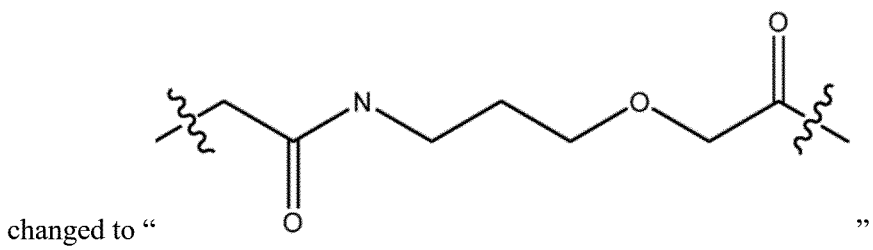"

Column 34, Lines 63-66, "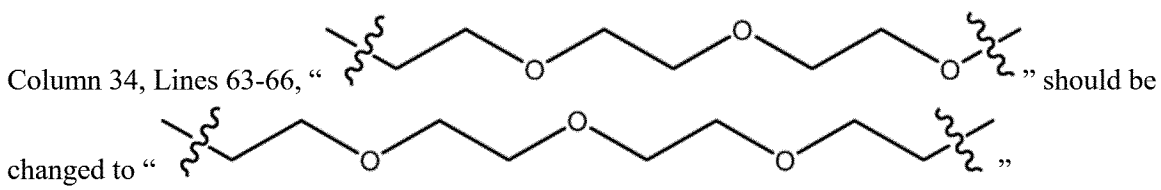" should be changed to ""

Column 44, Line 8, "Co" should be changed to "$C_0$"

Column 44, Line 10, "Co" should be changed to "$C_0$"

Column 57, Line 48, "25-50 m" should be changed to "25-50 μg"

Column 57, Line 49, "ERa" should be changed to "ERα"

Column 57, Line 50, "(3-actin" should be changed to "β-actin"

Column 57, Line 50, "ERa" should be changed to "ERα"

Column 57, Line 52, "(3-actin" should be changed to "β-actin"

CERTIFICATE OF CORRECTION (continued)
U.S. Pat. No. 11,981,672 B2

In the Claims

Claim 1, Column 58, Line 50 to 67 the following structures and text should be deleted:

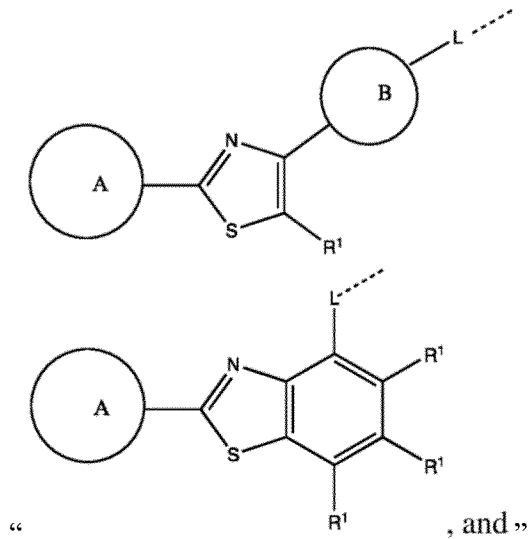

" 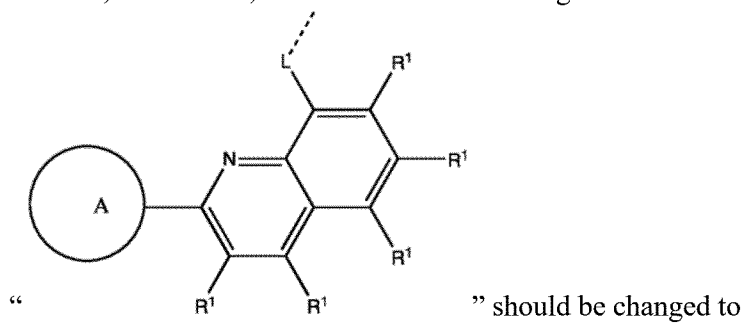 , and "

Claim 1, Column 59, Line 1 to 12 the following structure:

" 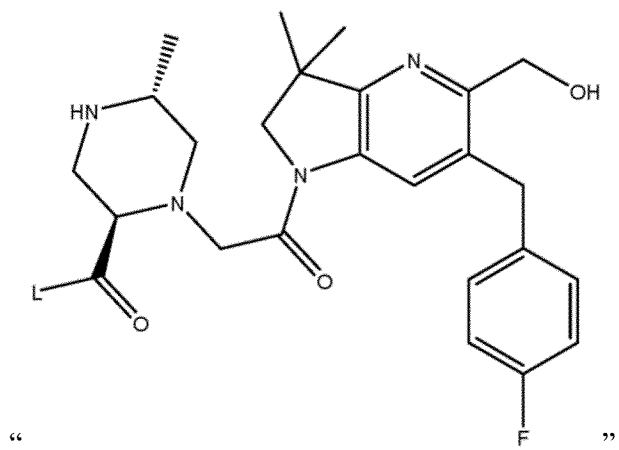 " should be changed to

" [structure image] "

Claim 5, Column 61, Line 21, "$SO_2R^{L3}$" should be changed to "$SONR^{L3}$"

Claim 5, Column 61, Line 22, "$NR^{L3}(=NCN)NR^{L4}$" should be changed to "$NR^{L3}C(=NCN)NR^{L4}$"

CERTIFICATE OF CORRECTION (continued)

Claim 5, Column 61, Line 23, "$NR^{13}C(C=NO_2)NR^{L4}$" should be changed to "$NR^{L3}C(=CNO_2)NR^{L4}$"

Claim 13, Column 67, Lines 10-25, the following structure:

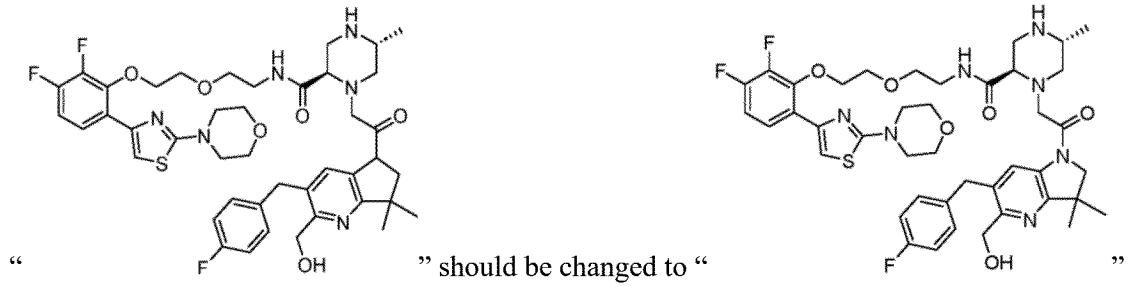

" should be changed to "                                                                    "

Claim 13, Column 67, Lines 40-53, the following structure:

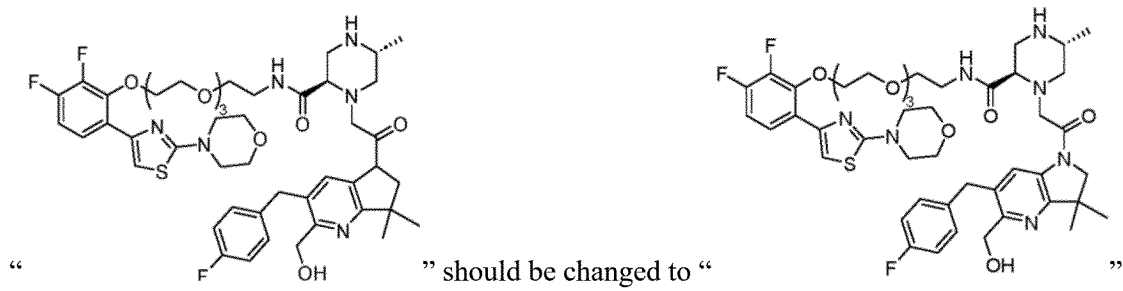

" should be changed to "                                                                    "

Claim 13, Column 67, Lines 54-66, the following structure:

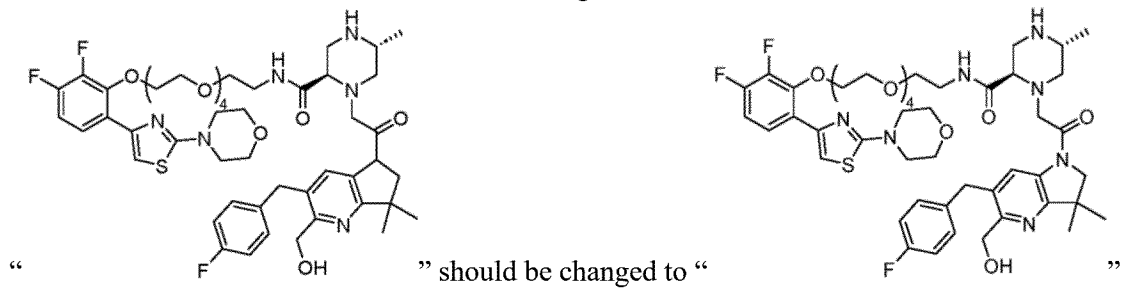

" should be changed to "                                                                    "

Claim 13, Column 68, Lines 16-30, the following structure:

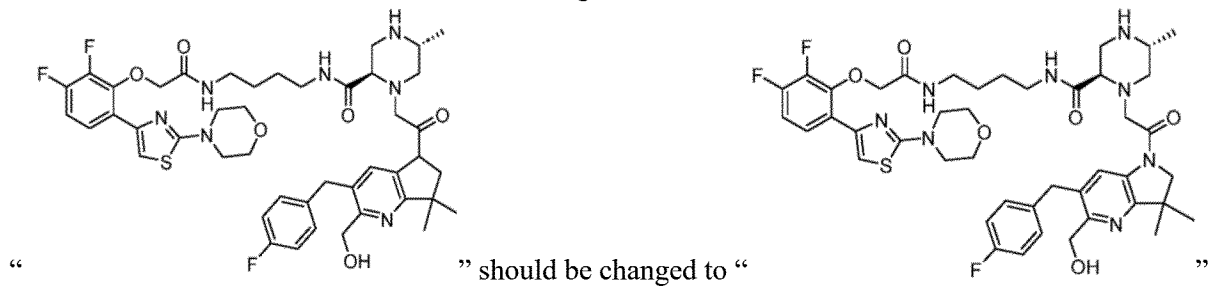

" should be changed to "                                                                    "